United States Patent (10) Patent No.: US 9,700,431 B2
Nebosky et al. (45) Date of Patent: Jul. 11, 2017

(54) ORTHOPAEDIC IMPLANT WITH POROUS STRUCTURAL MEMBER

(71) Applicant: SMed-TA/TD, LLC, Columbia City, IN (US)

(72) Inventors: Paul S. Nebosky, Fort Wayne, IN (US); Gregory C. Stalcup, Columbia City, IN (US)

(73) Assignee: SMed-TA/TD, LLC, Columbia City, IN (US)

( * ) Notice: Subject to any disclaimer, the term of this patent is extended or adjusted under 35 U.S.C. 154(b) by 119 days.

(21) Appl. No.: 14/637,142

(22) Filed: Mar. 3, 2015

(65) Prior Publication Data
US 2015/0238324 A1    Aug. 27, 2015

Related U.S. Application Data

(63) Continuation-in-part of application No. 12/540,515, filed on Aug. 13, 2009, now abandoned.
(Continued)

(51) Int. Cl.
*A61F 2/44* (2006.01)
*A61F 2/30* (2006.01)

(52) U.S. Cl.
CPC ............ *A61F 2/447* (2013.01); *A61F 2/3094* (2013.01); *A61F 2/4465* (2013.01); *A61F 2/30965* (2013.01); *A61F 2002/305* (2013.01); *A61F 2002/3008* (2013.01); *A61F 2002/30028* (2013.01); *A61F 2002/3097* (2013.01); *A61F 2002/30261* (2013.01); *A61F 2002/30322* (2013.01); *A61F 2002/30387* (2013.01); *A61F 2002/30451* (2013.01);
(Continued)

(58) Field of Classification Search
None
See application file for complete search history.

(56) References Cited

U.S. PATENT DOCUMENTS 3,662,405 A    5/1972    Bortz et al.
3,683,421 A    8/1972    Martinie
(Continued)

FOREIGN PATENT DOCUMENTS

DE    4211345 C1    11/1993
DE    4423020 A1    1/1996
(Continued)

OTHER PUBLICATIONS

International Search Report dated Sep. 28, 2009 of International Searching Authority for Application No. PCT/US2009/053724 (2 pages).
(Continued)

*Primary Examiner* — Ellen C Hammond
*Assistant Examiner* — Stuart S Bray
(74) *Attorney, Agent, or Firm* — Taylor IP, P.C.

(57) ABSTRACT

An orthopedic implant includes an implant body having a first surface with a first peak, a second surface opposite the first surface, and a cavity formed therein that extends through the first surface and second surface. The implant body is substantially non-porous. A load bearing member comprising a substantially porous material is held within the cavity. The load bearing member has a first contact surface that extends out of the cavity past the first peak of the first surface.

13 Claims, 11 Drawing Sheets

Related U.S. Application Data

(60) Provisional application No. 61/088,460, filed on Aug. 13, 2008.

(52) U.S. Cl.
CPC .............. *A61F 2002/30492* (2013.01); *A61F 2002/30599* (2013.01); *A61F 2002/30622* (2013.01); *A61F 2002/30677* (2013.01); *A61F 2002/30733* (2013.01); *A61F 2002/30841* (2013.01); *A61F 2002/30971* (2013.01); *A61F 2002/30981* (2013.01); *A61F 2002/4475* (2013.01); *A61F 2310/00017* (2013.01); *A61F 2310/00023* (2013.01); *A61F 2310/00203* (2013.01); *A61F 2310/00293* (2013.01)

(56) References Cited

U.S. PATENT DOCUMENTS

| | | |
|---|---|---|
| 3,855,638 A | 12/1974 | Pilliar |
| 3,867,728 A | 2/1975 | Stubstad et al. |
| 4,011,602 A | 3/1977 | Rybicki et al. |
| 4,060,081 A | 11/1977 | Yannas et al. |
| 4,156,943 A | 6/1979 | Collier |
| 4,222,128 A | 9/1980 | Tomonaga et al. |
| 4,450,150 A | 5/1984 | Sidman |
| 4,453,537 A | 6/1984 | Spitzer |
| 4,485,097 A | 11/1984 | Bell |
| 4,520,821 A | 6/1985 | Schmidt et al. |
| 4,608,052 A | 8/1986 | Van Kampen et al. |
| 4,609,551 A | 9/1986 | Caplan et al. |
| 4,620,327 A | 11/1986 | Caplan et al. |
| 4,644,627 A | 2/1987 | Palazzo |
| 4,660,755 A | 4/1987 | Farling et al. |
| 4,737,411 A | 4/1988 | Graves, Jr. et al. |
| 4,769,041 A | 9/1988 | Morscher |
| 4,846,834 A | 7/1989 | Von Recum et al. |
| 4,858,603 A | 8/1989 | Clemow et al. |
| 4,936,859 A | 6/1990 | Morscher et al. |
| 4,976,738 A | 12/1990 | Frey et al. |
| 5,030,233 A | 7/1991 | Ducheyne |
| 5,041,107 A | 8/1991 | Heil, Jr. |
| 5,084,051 A | 1/1992 | Tormala et al. |
| 5,092,898 A | 3/1992 | Bekki et al. |
| 5,100,392 A | 3/1992 | Orth et al. |
| 5,104,410 A | 4/1992 | Chowdhary |
| 5,190,550 A | 3/1993 | Miller et al. |
| 5,197,985 A | 3/1993 | Caplan et al. |
| 5,204,055 A | 4/1993 | Sachs et al. |
| 5,219,363 A | 6/1993 | Crowninshield et al. |
| 5,226,914 A | 7/1993 | Caplan et al. |
| 5,281,210 A | 1/1994 | Burke et al. |
| 5,282,861 A | 2/1994 | Kaplan |
| 5,306,309 A | 4/1994 | Wagner et al. |
| 5,328,765 A | 7/1994 | Anderson et al. |
| 5,370,690 A | 12/1994 | Barrett |
| 5,380,328 A | 1/1995 | Morgan |
| 5,443,471 A | 8/1995 | Swajger |
| 5,458,643 A | 10/1995 | Oka et al. |
| 5,462,362 A | 10/1995 | Yuhta et al. |
| 5,490,962 A | 2/1996 | Cima et al. |
| 5,496,372 A | 3/1996 | Hamamoto et al. |
| 5,514,182 A | 5/1996 | Shea |
| 5,518,680 A | 5/1996 | Cima et al. |
| 5,531,750 A | 7/1996 | Even-Esh |
| 5,534,028 A | 7/1996 | Bao et al. |
| 5,537,851 A | 7/1996 | Sheu et al. |
| 5,549,700 A | 8/1996 | Graham et al. |
| 5,571,187 A | 11/1996 | Devanathan |
| 5,593,443 A | 1/1997 | Carter et al. |
| 5,637,175 A | 6/1997 | Feygin et al. |
| 5,641,323 A | 6/1997 | Caldarise |
| 5,702,449 A | 12/1997 | McKay |
| 5,730,817 A | 3/1998 | Feygin et al. |
| 5,732,469 A | 3/1998 | Hamamoto et al. |
| 5,750,103 A | 5/1998 | Cherksey |
| 5,769,897 A | 6/1998 | Harle |
| 5,776,199 A | 7/1998 | Michelson |
| 5,800,828 A | 9/1998 | Dionne et al. |
| 5,807,406 A | 9/1998 | Brauker et al. |
| 5,848,989 A | 12/1998 | Villani |
| 5,849,015 A | 12/1998 | Haywood et al. |
| 5,869,170 A | 2/1999 | Cima et al. |
| 5,871,484 A | 2/1999 | Spievack et al. |
| 5,876,550 A | 3/1999 | Feygin et al. |
| 5,879,406 A | 3/1999 | Lilley |
| 5,916,269 A | 6/1999 | Serbousek et al. |
| 5,971,985 A | 10/1999 | Carchidi et al. |
| 5,989,250 A | 11/1999 | Wagner et al. |
| 6,010,336 A | 1/2000 | Shimotoso et al. |
| 6,037,519 A * | 3/2000 | McKay ............... A61F 2/446 423/305 |
| 6,045,581 A | 4/2000 | Burkinshaw |
| 6,110,179 A | 8/2000 | Flivik et al. |
| 6,136,029 A | 10/2000 | Johnson et al. |
| 6,136,031 A | 10/2000 | Middleton |
| 6,139,574 A | 10/2000 | Vacanti et al. |
| 6,143,035 A | 11/2000 | McDowell |
| 6,159,247 A | 12/2000 | Klawitter et al. |
| 6,176,874 B1 | 1/2001 | Vacanti et al. |
| 6,238,435 B1 | 5/2001 | Meulink et al. |
| 6,283,997 B1 | 9/2001 | Garg et al. |
| 6,290,726 B1 | 9/2001 | Pope et al. |
| 6,306,424 B1 | 10/2001 | Vyakarnam et al. |
| 6,315,797 B1 | 11/2001 | Middleton |
| 6,322,564 B1 | 11/2001 | Surma |
| 6,328,765 B1 | 12/2001 | Hardwick et al. |
| 6,333,029 B1 | 12/2001 | Vyakarnam et al. |
| 6,337,198 B1 | 1/2002 | Levene et al. |
| 6,365,149 B2 | 4/2002 | Vyakarnam et al. |
| 6,379,391 B1 | 4/2002 | Masini |
| 6,395,011 B1 | 5/2002 | Johanson et al. |
| 6,409,764 B1 | 6/2002 | White et al. |
| 6,419,704 B1 | 7/2002 | Ferree |
| 6,423,095 B1 * | 7/2002 | Van Hoeck ............. A61F 2/442 606/247 |
| 6,423,252 B1 | 7/2002 | Chun et al. |
| 6,425,921 B1 | 7/2002 | Grundei et al. |
| 6,440,734 B1 | 8/2002 | Pykett et al. |
| 6,454,811 B1 | 9/2002 | Sherwood et al. |
| 6,458,162 B1 * | 10/2002 | Koblish ............... A61B 17/866 423/305 |
| 6,461,385 B1 | 10/2002 | Gayer et al. |
| 6,471,689 B1 | 10/2002 | Joseph et al. |
| 6,471,993 B1 | 10/2002 | Shastri et al. |
| 6,475,137 B1 | 11/2002 | Elist |
| 6,494,916 B1 | 12/2002 | Babalola et al. |
| 6,514,514 B1 | 2/2003 | Atkinson et al. |
| 6,520,993 B2 | 2/2003 | James et al. |
| 6,526,984 B1 | 3/2003 | Nilsson et al. |
| 6,527,810 B2 | 3/2003 | Johnson et al. |
| 6,530,958 B1 | 3/2003 | Cima et al. |
| 6,533,818 B1 | 3/2003 | Weber et al. |
| 6,534,084 B1 | 3/2003 | Vyakarnam et al. |
| 6,544,472 B1 | 4/2003 | Compton et al. |
| 6,547,824 B1 | 4/2003 | Price |
| 6,551,290 B1 | 4/2003 | Elsberry et al. |
| 6,554,857 B1 | 4/2003 | Zilla et al. |
| 6,565,572 B2 | 5/2003 | Chappius |
| 6,571,130 B1 | 5/2003 | Ljungstroem et al. |
| 6,599,322 B1 | 7/2003 | Amrich et al. |
| 6,610,095 B1 | 8/2003 | Pope et al. |
| 6,626,950 B2 | 9/2003 | Brown et al. |
| 6,635,049 B1 | 10/2003 | Robinson et al. |
| 6,645,251 B2 | 11/2003 | Salehi et al. |
| 6,656,489 B1 | 12/2003 | Mahmood et al. |
| 6,660,040 B2 | 12/2003 | Chan et al. |
| 6,673,108 B2 | 1/2004 | Zilla et al. |
| 6,682,567 B1 | 1/2004 | Schroeder |
| 6,692,528 B2 | 2/2004 | Ward et al. |
| 6,709,463 B1 | 3/2004 | Pope et al. |
| 6,709,464 B2 | 3/2004 | Scott et al. |
| 6,712,850 B2 | 3/2004 | Vyakarnam et al. |
| 6,723,120 B2 | 4/2004 | Yan |

(56) References Cited

U.S. PATENT DOCUMENTS

| | | |
|---|---|---|
| 6,736,850 B2 | 5/2004 | Davis |
| 6,749,636 B2 | 6/2004 | Michelson |
| 6,758,863 B2 | 7/2004 | Estes et al. |
| 6,783,546 B2 | 8/2004 | Zucherman et al. |
| 6,818,620 B2 | 11/2004 | Bhatnagar |
| 6,852,272 B2 | 2/2005 | Artz et al. |
| 6,863,899 B2 | 3/2005 | Koblish et al. |
| 6,866,685 B2 | 3/2005 | Chan et al. |
| 6,881,413 B1 | 4/2005 | Bartholeyns |
| 6,893,465 B2 | 5/2005 | Huang |
| 6,913,623 B1 | 7/2005 | Zhu |
| 6,916,321 B2 | 7/2005 | TenHuisen et al. |
| 6,958,078 B2 | 10/2005 | Goel et al. |
| 6,969,383 B2 | 11/2005 | Hildebrand |
| 6,979,353 B2 * | 12/2005 | Bresina ............... A61B 17/1637 623/17.11 |
| 6,989,033 B1 | 1/2006 | Schmidt |
| 6,993,406 B1 | 1/2006 | Cesarano, III et al. |
| 7,018,416 B2 * | 3/2006 | Hanson ............... A61B 17/1671 623/17.16 |
| 7,018,418 B2 | 3/2006 | Amrich et al. |
| 7,052,710 B2 | 5/2006 | Giordano et al. |
| 7,077,867 B1 | 7/2006 | Pope et al. |
| 7,087,086 B2 | 8/2006 | Li et al. |
| 7,087,200 B2 | 8/2006 | Taboas et al. |
| 7,090,668 B1 | 8/2006 | U et al. |
| 7,094,371 B2 | 8/2006 | Lo |
| 7,108,828 B2 | 9/2006 | Lefebvre et al. |
| 7,112,223 B2 | 9/2006 | Davis |
| 7,128,762 B2 | 10/2006 | Middleton |
| D533,277 S * | 12/2006 | Blain ............... A61B 17/1671 D24/155 |
| 7,174,282 B2 | 2/2007 | Hollister et al. |
| 7,189,409 B2 | 3/2007 | Pirhonen et al. |
| 7,192,440 B2 | 3/2007 | Andreas et al. |
| D539,934 S * | 4/2007 | Blain ............... A61B 17/1671 D25/155 |
| 7,208,222 B2 | 4/2007 | Rolfe et al. |
| D541,940 S * | 5/2007 | Blain ............... A61B 17/1671 D24/155 |
| 7,226,612 B2 | 6/2007 | Sohier et al. |
| 7,238,186 B2 | 7/2007 | Zdeblick et al. |
| 7,238,363 B2 | 7/2007 | Mansouri et al. |
| 7,250,055 B1 | 7/2007 | Vanderwalle |
| 7,250,060 B2 | 7/2007 | Trieu |
| 7,255,713 B2 | 8/2007 | Malek |
| 7,300,439 B2 | 11/2007 | May |
| D564,095 S * | 3/2008 | Blain ............... A61B 17/1671 D24/155 |
| D566,276 S * | 4/2008 | Blain ............... A61B 17/1671 D24/155 |
| 7,354,452 B2 | 4/2008 | Foley |
| 7,537,617 B2 | 5/2009 | Bindsell et al. |
| 7,537,664 B2 | 5/2009 | O'Neill et al. |
| D594,986 S * | 6/2009 | Miles ............... A61B 17/1671 D24/155 |
| D599,019 S * | 8/2009 | Pimenta ............... A61B 17/1671 D24/155 |
| 7,575,572 B2 | 8/2009 | Sweeney |
| 7,632,228 B2 | 12/2009 | Brauker et al. |
| 7,632,338 B2 | 12/2009 | Cipollini |
| 7,666,230 B2 | 2/2010 | Orban et al. |
| 7,674,426 B2 | 3/2010 | Grohowski, Jr. |
| 7,674,477 B1 | 3/2010 | Schmid et al. |
| D616,546 S * | 5/2010 | Vraney ............... A61B 17/1671 D24/155 |
| 7,717,956 B2 | 5/2010 | Lang |
| D619,719 S * | 7/2010 | Pannu ............... A61B 17/1671 D24/155 |
| D620,114 S * | 7/2010 | Pannu ............... A61B 17/1671 D24/155 |
| D620,115 S * | 7/2010 | Pannu ............... A61B 17/1671 D24/155 |
| D620,116 S * | 7/2010 | Pannu ............... A61B 17/1671 D24/155 |
| D621,509 S * | 8/2010 | Lovell ............... A61B 17/1671 D24/155 |
| D627,467 S * | 11/2010 | Pannu ............... A61B 17/1671 D24/155 |
| D627,468 S * | 11/2010 | Richter ............... A61B 17/1671 D24/155 |
| 7,833,271 B2 * | 11/2010 | Mitchell ............... A61F 2/4465 623/17.11 |
| 7,875,080 B2 | 1/2011 | Puno et al. |
| 7,909,870 B2 * | 3/2011 | Kraus ............... A61F 2/44 623/17.11 |
| 7,963,995 B2 * | 6/2011 | Richelsoph ............. A61F 2/442 606/90 |
| 8,062,372 B2 * | 11/2011 | Tsuang ............... A61F 2/4455 623/17.11 |
| 8,066,750 B2 * | 11/2011 | Oi ............... A61B 17/7059 606/289 |
| 8,147,521 B1 * | 4/2012 | Cornwall ............. A61B 17/7001 606/265 |
| D671,645 S * | 11/2012 | Curran ............... A61B 17/1671 D24/155 |
| D674,092 S * | 1/2013 | Lovell ............... A61B 17/1671 D24/155 |
| 8,496,706 B2 * | 7/2013 | Ragab ............... A61F 2/4425 623/17.11 |
| 8,568,482 B2 * | 10/2013 | Kraus ............... A61F 2/44 606/914 |
| 8,623,088 B1 * | 1/2014 | Tohmeh ............... A61F 2/4455 623/17.11 |
| D770,045 S * | 10/2016 | Curran ............... A61B 17/1671 D24/155 |
| 2001/0038848 A1 | 11/2001 | Donda et al. |
| 2001/0039455 A1 | 11/2001 | Simon et al. |
| 2002/0022884 A1 | 2/2002 | Mansmann |
| 2002/0029083 A1 | 3/2002 | Zucherman et al. |
| 2002/0035400 A1 | 3/2002 | Bryan et al. |
| 2002/0062154 A1 | 5/2002 | Ayers |
| 2002/0072798 A1 | 6/2002 | Riesle et al. |
| 2002/0091447 A1 | 7/2002 | Shimp et al. |
| 2002/0106393 A1 | 8/2002 | Bianchi et al. |
| 2002/0128715 A1 | 9/2002 | Bryan et al. |
| 2002/0143402 A1 | 10/2002 | Steinberg |
| 2002/0161447 A1 | 10/2002 | Salehi et al. |
| 2002/0182241 A1 | 12/2002 | Borenstein et al. |
| 2002/0183850 A1 | 12/2002 | Felt et al. |
| 2002/0197178 A1 | 12/2002 | Yan |
| 2003/0003127 A1 | 1/2003 | Brown et al. |
| 2003/0004578 A1 | 1/2003 | Brown et al. |
| 2003/0006534 A1 | 1/2003 | Taboas et al. |
| 2003/0012805 A1 | 1/2003 | Chen et al. |
| 2003/0023311 A1 | 1/2003 | Trieu |
| 2003/0055506 A1 | 3/2003 | Stoy et al. |
| 2003/0060886 A1 | 3/2003 | Van Hoeck et al. |
| 2003/0060891 A1 | 3/2003 | Shah |
| 2003/0069465 A1 | 4/2003 | Benkowski et al. |
| 2003/0097182 A1 | 5/2003 | Buchman et al. |
| 2003/0105527 A1 | 6/2003 | Bresina |
| 2003/0114934 A1 | 6/2003 | Steinberg |
| 2003/0114936 A1 | 6/2003 | Sherwood et al. |
| 2003/0118649 A1 | 6/2003 | Gao et al. |
| 2003/0120344 A1 | 6/2003 | Michelson |
| 2003/0125739 A1 * | 7/2003 | Bagga ............... A61F 2/4455 606/247 |
| 2003/0130743 A1 | 7/2003 | Scott et al. |
| 2003/0139809 A1 | 7/2003 | Worst et al. |
| 2003/0171738 A1 | 9/2003 | Konieczynski et al. |
| 2003/0171820 A1 | 9/2003 | Wilshaw et al. |
| 2003/0180171 A1 | 9/2003 | Artz et al. |
| 2003/0187513 A1 | 10/2003 | Durniak |
| 2003/0203002 A1 | 10/2003 | Murphy et al. |
| 2003/0206928 A1 | 11/2003 | Tormala et al. |
| 2003/0208274 A1 | 11/2003 | Davis |
| 2004/0024470 A1 | 2/2004 | Giordano et al. |
| 2004/0034357 A1 | 2/2004 | Beane et al. |
| 2004/0034427 A1 | 2/2004 | Goel et al. |
| 2004/0063206 A1 | 4/2004 | Rowley et al. |

(56) References Cited

U.S. PATENT DOCUMENTS

| | | |
|---|---|---|
| 2004/0073197 A1 | 4/2004 | Kim |
| 2004/0115172 A1 | 6/2004 | Bianchi et al. |
| 2004/0126405 A1 | 7/2004 | Sahatjian et al. |
| 2004/0147905 A1 | 7/2004 | Krumme |
| 2004/0153165 A1 | 8/2004 | Li et al. |
| 2004/0180072 A1 | 9/2004 | Tunc et al. |
| 2004/0191106 A1 | 9/2004 | O'Neill et al. |
| 2004/0191292 A1 | 9/2004 | Chou |
| 2004/0193273 A1 | 9/2004 | Huang |
| 2004/0199260 A1 | 10/2004 | Pope et al. |
| 2004/0210274 A1 | 10/2004 | Bauhahn et al. |
| 2004/0210316 A1 | 10/2004 | King et al. |
| 2004/0215173 A1 | 10/2004 | Kunst |
| 2004/0225360 A1 | 11/2004 | Malone |
| 2004/0249463 A1 | 12/2004 | Bindseil et al. |
| 2004/0258732 A1* | 12/2004 | Shikinami ............ A61L 27/446 424/426 |
| 2004/0265350 A1 | 12/2004 | Sambrook et al. |
| 2004/0267263 A1 | 12/2004 | May |
| 2005/0015059 A1 | 1/2005 | Sweeney |
| 2005/0015150 A1 | 1/2005 | Lee |
| 2005/0021084 A1 | 1/2005 | Lu et al. |
| 2005/0049715 A1 | 3/2005 | Ito et al. |
| 2005/0049716 A1 | 3/2005 | Wagener et al. |
| 2005/0055099 A1 | 3/2005 | Ku |
| 2005/0058684 A1 | 3/2005 | Shanley et al. |
| 2005/0059972 A1 | 3/2005 | Biscup |
| 2005/0085888 A1 | 4/2005 | Andreas et al. |
| 2005/0100470 A1 | 5/2005 | Lefebvre et al. |
| 2005/0100578 A1 | 5/2005 | Schmid et al. |
| 2005/0112397 A1 | 5/2005 | Rolfe et al. |
| 2005/0119753 A1 | 6/2005 | McGahan et al. |
| 2005/0125073 A1 | 6/2005 | Orban et al. |
| 2005/0137707 A1 | 6/2005 | Malek |
| 2005/0143822 A1 | 6/2005 | Paul |
| 2005/0159819 A1 | 7/2005 | McCormack et al. |
| 2005/0171611 A1 | 8/2005 | Stoy et al. |
| 2005/0175703 A1 | 8/2005 | Hunter et al. |
| 2005/0177238 A1 | 8/2005 | Khandkar et al. |
| 2005/0177247 A1 | 8/2005 | Canham et al. |
| 2005/0182494 A1 | 8/2005 | Schmid |
| 2005/0187555 A1 | 8/2005 | Biedermann et al. |
| 2005/0192669 A1 | 9/2005 | Zdeblick et al. |
| 2005/0197654 A1 | 9/2005 | Edman et al. |
| 2005/0202371 A1 | 9/2005 | McGuire |
| 2005/0220837 A1 | 10/2005 | Disegi et al. |
| 2005/0222688 A1 | 10/2005 | Zilla et al. |
| 2005/0228503 A1 | 10/2005 | Gundolf |
| 2005/0246032 A1 | 11/2005 | Bokros et al. |
| 2005/0271694 A1 | 12/2005 | Mansouri et al. |
| 2005/0272153 A1 | 12/2005 | Xuenong et al. |
| 2005/0273082 A1 | 12/2005 | Olsen |
| 2005/0273178 A1 | 12/2005 | Boyan et al. |
| 2006/0002810 A1 | 1/2006 | Grohowski, Jr. |
| 2006/0015186 A1 | 1/2006 | Isaac |
| 2006/0047341 A1 | 3/2006 | Trieu |
| 2006/0057737 A1 | 3/2006 | Santini, Jr. et al. |
| 2006/0064170 A1 | 3/2006 | Smith et al. |
| 2006/0064172 A1 | 3/2006 | Trieu |
| 2006/0083730 A1 | 4/2006 | Kusanagi et al. |
| 2006/0093646 A1 | 5/2006 | Cima et al. |
| 2006/0100706 A1 | 5/2006 | Shadduck et al. |
| 2006/0100716 A1 | 5/2006 | Lerf |
| 2006/0105015 A1 | 5/2006 | Perla et al. |
| 2006/0111782 A1 | 5/2006 | Petersen |
| 2006/0111785 A1 | 5/2006 | O'Neil |
| 2006/0121609 A1 | 6/2006 | Yannas et al. |
| 2006/0129242 A1 | 6/2006 | Bergeron et al. |
| 2006/0141012 A1 | 6/2006 | Gingras |
| 2006/0149220 A1 | 7/2006 | Ullestad et al. |
| 2006/0149386 A1 | 7/2006 | Clark et al. |
| 2006/0173542 A1 | 8/2006 | Shikinami |
| 2006/0178744 A1 | 8/2006 | de Villiers et al. |
| 2006/0193885 A1 | 8/2006 | Leonard Neethling et al. |
| 2006/0195188 A1 | 8/2006 | O'Driscoll et al. |
| 2006/0200166 A1 | 9/2006 | Hanson et al. |
| 2006/0204581 A1 | 9/2006 | Gower et al. |
| 2006/0229715 A1 | 10/2006 | Istephanous et al. |
| 2006/0235534 A1 | 10/2006 | Gertzman et al. |
| 2006/0241593 A1 | 10/2006 | Sherman et al. |
| 2006/0264950 A1 | 11/2006 | Nelson et al. |
| 2006/0271022 A1 | 11/2006 | Steinbach et al. |
| 2006/0271201 A1 | 11/2006 | Kumar et al. |
| 2006/0276900 A1 | 12/2006 | Carpenter |
| 2006/0282166 A1 | 12/2006 | Molz et al. |
| 2006/0287689 A1 | 12/2006 | Debruyne et al. |
| 2006/0289388 A1 | 12/2006 | Yang et al. |
| 2006/0293757 A1 | 12/2006 | McKay et al. |
| 2007/0016163 A1 | 1/2007 | Santini, Jr. et al. |
| 2007/0026069 A1 | 2/2007 | Shastri et al. |
| 2007/0038299 A1 | 2/2007 | Stone et al. |
| 2007/0041952 A1 | 2/2007 | Guilak et al. |
| 2007/0043446 A1 | 2/2007 | Murray |
| 2007/0077267 A1 | 4/2007 | Molz, IV et al. |
| 2007/0105222 A1 | 5/2007 | Wolfinbarger et al. |
| 2007/0116734 A1 | 5/2007 | Akash |
| 2007/0123843 A1 | 5/2007 | Gill |
| 2007/0138042 A1 | 6/2007 | Wood |
| 2007/0141105 A1 | 6/2007 | Stein et al. |
| 2007/0141533 A1 | 6/2007 | Ford et al. |
| 2007/0150063 A1 | 6/2007 | Ruberte et al. |
| 2007/0150064 A1 | 6/2007 | Ruberte et al. |
| 2007/0150068 A1 | 6/2007 | Dong et al. |
| 2007/0160681 A1 | 7/2007 | Park et al. |
| 2007/0161986 A1 | 7/2007 | Levy |
| 2007/0162110 A1 | 7/2007 | Dave |
| 2007/0166348 A1 | 7/2007 | Van Dyke |
| 2007/0168021 A1 | 7/2007 | Holmes, Jr. et al. |
| 2007/0185580 A1 | 8/2007 | Posel |
| 2007/0185585 A1 | 8/2007 | Bracy et al. |
| 2007/0190880 A1 | 8/2007 | Dubrow et al. |
| 2007/0191963 A1 | 8/2007 | Winterbottom et al. |
| 2007/0196419 A1 | 8/2007 | Teller et al. |
| 2007/0202145 A1 | 8/2007 | Ghabrial et al. |
| 2007/0203584 A1 | 8/2007 | Bandyopadhyay et al. |
| 2007/0208420 A1 | 9/2007 | Ameer et al. |
| 2007/0213827 A1 | 9/2007 | Arramon |
| 2007/0233071 A1 | 10/2007 | Dewey et al. |
| 2007/0243225 A1 | 10/2007 | McKay |
| 2007/0250169 A1 | 10/2007 | Lang |
| 2007/0255262 A1 | 11/2007 | Haase |
| 2007/0255416 A1 | 11/2007 | Melkent et al. |
| 2007/0260320 A1 | 11/2007 | Peterman et al. |
| 2007/0270859 A1 | 11/2007 | Companioni et al. |
| 2007/0293948 A1 | 12/2007 | Bagga et al. |
| 2008/0004704 A1 | 1/2008 | Katz |
| 2008/0015578 A1 | 1/2008 | Erickson et al. |
| 2008/0046082 A1 | 2/2008 | Lee |
| 2008/0065218 A1 | 3/2008 | O'Neil |
| 2008/0077247 A1 | 3/2008 | Murillo et al. |
| 2008/0109083 A1 | 5/2008 | Van Hoeck et al. |
| 2008/0119945 A1 | 5/2008 | Frigg |
| 2008/0147193 A1* | 6/2008 | Matthis ................ A61F 2/4425 623/17.16 |
| 2008/0188940 A1* | 8/2008 | Cohen ................. A61F 2/4465 623/17.16 |
| 2008/0200985 A1* | 8/2008 | Robie .................. A61F 2/4455 623/17.16 |
| 2008/0262622 A1* | 10/2008 | Butler ................... A61F 2/442 623/17.16 |
| 2008/0288074 A1* | 11/2008 | O'Neil .................. A61F 2/442 623/17.16 |
| 2008/0306609 A1 | 12/2008 | Lee et al. |
| 2009/0005872 A1* | 1/2009 | Moumene .............. A61F 2/442 623/17.16 |
| 2009/0005874 A1 | 1/2009 | Fleischmann et al. |
| 2009/0024224 A1 | 1/2009 | Chen et al. |
| 2009/0030399 A1 | 1/2009 | Raiszadeh |
| 2009/0132051 A1* | 5/2009 | Moskowitz .......... A61F 2/4425 623/17.16 |
| 2009/0222098 A1* | 9/2009 | Trieu .................... A61F 2/442 623/17.16 |

(56) References Cited

U.S. PATENT DOCUMENTS

| | | | |
|---|---|---|---|
| 2009/0228109 A1* | 9/2009 | Pointillant | A61F 2/442 623/17.16 |
| 2009/0248162 A1* | 10/2009 | Peckham | A61F 2/4455 623/17.16 |
| 2009/0254182 A1* | 10/2009 | Kovarik | A61F 2/4611 623/17.11 |
| 2009/0270986 A1* | 10/2009 | Christensen | A61F 2/4425 623/17.14 |
| 2009/0270988 A1* | 10/2009 | Snell | A61F 2/30771 623/17.16 |
| 2009/0270991 A1* | 10/2009 | Michelson | A61F 2/4455 623/17.16 |
| 2009/0270992 A1* | 10/2009 | Gerber | A61F 2/441 623/17.16 |
| 2009/0276049 A1* | 11/2009 | Weiland | A61F 2/4465 623/17.16 |
| 2009/0281517 A1* | 11/2009 | Lambrecht | A61B 17/70 604/500 |
| 2009/0281625 A1* | 11/2009 | Enayati | A61F 2/446 623/17.11 |
| 2009/0292363 A1* | 11/2009 | Goldfarb | A61F 2/442 623/17.16 |
| 2009/0317278 A1* | 12/2009 | Kokubo | A61F 2/4455 419/2 |
| 2009/0326657 A1* | 12/2009 | Grinberg | A61F 2/4425 623/17.16 |
| 2010/0003639 A1 | 1/2010 | Salvi et al. | |
| 2010/0016970 A1* | 1/2010 | Kapitan | A61F 2/442 623/17.12 |
| 2010/0042167 A1 | 2/2010 | Nebosky et al. | |
| 2010/0042213 A1 | 2/2010 | Nebosky et al. | |
| 2010/0042214 A1 | 2/2010 | Nebosky et al. | |
| 2010/0042215 A1 | 2/2010 | Stalcup et al. | |
| 2010/0042218 A1* | 2/2010 | Nebosky | A61F 2/3094 623/17.12 |
| 2010/0042226 A1 | 2/2010 | Nebosky et al. | |
| 2010/0076559 A1* | 3/2010 | Bagga | A61F 2/4465 623/17.16 |
| 2010/0168798 A1* | 7/2010 | Clineff | A61L 27/446 606/279 |
| 2010/0190254 A1 | 7/2010 | Chian et al. | |
| 2010/0234966 A1 | 9/2010 | Lo | |
| 2010/0291286 A1 | 11/2010 | O'Neill et al. | |
| 2011/0012280 A1* | 1/2011 | Deslauriers | A61F 2/4465 264/45.7 |
| 2011/0064784 A1 | 3/2011 | Mullens et al. | |
| 2011/0066244 A1* | 3/2011 | Frasier | A61F 2/44 623/17.11 |
| 2011/0137418 A1* | 6/2011 | O'Neil | A61F 2/28 623/16.11 |
| 2011/0153028 A1 | 6/2011 | Albertorio | |
| 2011/0190888 A1 | 8/2011 | Bertele et al. | |
| 2011/0230970 A1* | 9/2011 | Lynn | A61F 2/442 623/17.16 |
| 2011/0313532 A1* | 12/2011 | Hunt | A61F 2/30767 623/18.11 |
| 2012/0303128 A1* | 11/2012 | Ullrich, Jr. | A61F 2/442 623/17.16 |
| 2012/0316650 A1 | 12/2012 | Ullrich, Jr. et al. | |
| 2013/0030529 A1* | 1/2013 | Hunt | A61F 2/30771 623/16.11 |
| 2015/0150689 A1* | 6/2015 | Wang | A61F 2/447 623/17.16 |
| 2015/0238324 A1* | 8/2015 | Nebosky | A61F 2/447 623/17.16 |

FOREIGN PATENT DOCUMENTS

| | | |
|---|---|---|
| DE | 693 28 047 T2 | 3/2000 |
| DE | 19904436 A1 | 8/2000 |
| DE | 10051438 A1 | 5/2002 |
| DE | 695 28 346 T2 | 9/2002 |
| DE | 10120330 A1 | 11/2002 |
| DE | 10157315 C1 | 8/2003 |
| EP | 0617931 A2 | 10/1994 |
| EP | 0827726 A2 | 3/1998 |
| EP | 1 273 312 A2 | 1/2003 |
| EP | 1 287 851 A1 | 3/2003 |
| EP | 1475057 A1 | 11/2004 |
| EP | 1806112 A1 | 7/2007 |
| FR | 2697155 A1 | 4/1994 |
| JP | 6007388 A | 1/1994 |
| JP | 7116184 A | 5/1995 |
| JP | 8173463 A | 7/1996 |
| JP | 2587625 B2 | 12/1996 |
| JP | 2002325781 A | 11/2002 |
| JP | 2005329179 A | 12/2005 |
| WO | 03084602 A2 | 10/2003 |
| WO | 03101504 A1 | 12/2003 |
| WO | 2005/047467 A2 | 5/2005 |
| WO | 2006/088480 A2 | 8/2006 |
| WO | 2006/135727 A2 | 12/2006 |
| WO | 2007/135444 A2 | 11/2007 |

OTHER PUBLICATIONS

International Search Report dated Sep. 28, 2009 of International Searching Authority for Application No. PCT/US2009/053735 (2 pages).
International Search Report dated Sep. 23, 2009 of International Searching Authority for Application No. PCT/US2009/053762 (2 pages).
International Search Report dated Oct. 14, 2009 of International Searching Authority for Application No. PCT/US2009/053751 (2 pages).
Joseph P. Vacanti, Martin A. Morse, W. Mark Saltzman, Abraham J. Domb, Antonio Perez-Atayde, and Robert Langer; article entitles "Selective Cell Transplantation Using Bioabsorbable Artifical Polymers as Matrices", Journal of Pediatric Surgery, vol. 23, No. 1, pp. 3-9, Jan. 1988, published by Grune & Stratton, Inc.
N.R. Boeree, J. Dove, J.J. Cooper, J. Knowles, and G.W. Hastings, article entitled "Development of a Degradable Composite for Orthopaedic Use: Mechanical Evaluation of an Hydroxyapatite-Polyhydroxybutyrate Composite Material", Biomaterials, vol. 14, No. 10, pp. 793-796, 1993, published by Butterworth-Heinemann Ltd.
R.B. Martin, M.W. Chapman, N.A. Sharkey, S.L. Zissimos, B. Bay, and E.C. Shors, article entitled "Bone Ingrowth and Mechanical Properties of Coralline Hydroxyapatite 1 Yr After Implantation", Biomaterials, vol. 14, No. 5, pp. 341-348, 1993, published by Butterworth-Heinemann Ltd.
Article entitled "Fractal" (nine pages), published on the Internet by the online encyclopedia Wikipedia; downloaded from the internet on Dec. 14, 2006 in the United States from the following address: http://en.wikipedia.org/wiki/Fractals.
Editor in Chief Sybil P. Parker, p. 799 (showing entries from "fp" to "fracture test") of McGraw-Hill Dictionary of Scientific and Technical Terms, Fifth Edition, published by McGraw-Hill, Inc., 1994, New York.
Office Action dated Oct. 31, 2008 in U.S. Appl. No. 10/980,425 (20 pages).
Office Action dated Oct. 20, 2006 in U.S. Appl. No. 11/060,377 (10 pages).
Written Opinion dated Sep. 28, 2009 of International Searching Authority for Application No. PCT/US2009/053724 (8 pages).
Written Opinion dated Sep. 28, 2009 of International Searching Authority for Application No. PCT/US2009/053735 (7 pages).
Written Opinion dated Sep. 23, 2009 of International Searching Authority for Application No. PCT/US2009/053762 (4 pages).
Written Opinion dated Oct. 14, 2009 of International Searching Authority for Application No. PCT/US2009/053751 (6 pages).
Article entitled "Rolled Threads" (3 pages), published on the Internet by the online encyclopedia Wikipedia; downloaded from the internet on Aug. 24, 2009 in the United States from the following address: http://en.wikipedia.org/wiki/File:American_Machinists_Handbook-2e—p23-v001.png.

(56) References Cited

OTHER PUBLICATIONS

Written Opinion dated Apr. 13, 2010 of International Searching Authority for Application No. PCT/US2009/055380 (8 pages).
Written Opinion dated Oct. 13, 2009 of International Searching Authority for Application No. PCT/US2009/055397 (9 pages).
Unknown Author, article entitled "MacroPore Resorbable Technology: An Overview", Scientific Data Series in Resorbable Fixation, MKT004 Rev. Jun. 2001, pp. 1-8; distributed by Medtronic Sofamor Danek, 1800 Pyramid Place, Memphis TN 38132, (Jun. 2001).
Ralph E. Holmes, M.D., Stefan M. Lemperle, M.D., and Christopher J. Calhoun, M.B.A., article entitled "Protected Bone Regeneration", Scientific Data Series in Resorbable Fixation, MKT003 Rev. Jun. 2001, pp. 1-10; distributed by Medtronic Sofamor Danek, 1800 Pyramid Place, Memphis TN 38132, (Jun. 2001).
D.R. Sumner, T.M. Turner, R.M. Urban, R.M. Leven, M. Hawkins, E.H. Nichols, J.M. McPherson, J.O. Galante, article entitled "Locally Delivered rhTGF-B2 Enhances Bone Ingrowth and Bone Regeneration at Local and Remote Sites of Skeletal Injury", Journal of Orthopaedic Research 19 (2001) pp. 85-94, published by Elsevier Science Ltd.
International Search Report dated May 18, 2005 of International Searching Authority for Application No. PCT/US2004/036997 (3 pages).
U.S. Appl. No. 08/048,408, filed Apr. 15, 1993 with U.S. Patent & Trademark Office (108 pages).
Preliminary Amendment dated Jul. 8, 1993 and filed in U.S. Appl. No. 08/048,408 with U.S. Patent & Trademark Office (12 pages).
Machine English translation of JP 2587625 (10 pages).
International Preliminary Report on Patentability dated May 8, 2006 of International Searching Authority for Application No. PCT/US2004/036997 (6 pages).
Written Opinion dated May 18, 2005 of International Searching Authority for Application No. PCT/US2004/036997 (5 pages).
Communication and supplementary European search report dated Nov. 14, 2008 from European Patent Office in application No. 04818642 (3 pages).
Office Action dated Jun. 25, 2010 from European Patent Office in application No. 04818642 (5 pages).
International Search Report dated Mar. 12, 2007 of International Searching Authority for PCT/US2005/019045 (3 pages).
International Preliminary Report on Patentability dated Aug. 21, 2007 of International Searching Authority for Application No. PCT/US2005/019045 (7 pages).
Written Opinion dated Mar. 12, 2007 of International Searching Authority for Application No. PCT/US2005/019045 (6 pages).
Office Action dated May 7, 2007 in U.S. Appl. No. 11/060,377 (13 pages).
Office Action dated Aug. 20, 2007 in U.S. Appl. No. 11/060,377 (3 pages).
Office Action dated Feb. 20, 2008 in U.S. Appl. No. 11/060,377 (5 pages).
Office Action dated Sep. 2, 2008 in U.S. Appl. No. 11/060,377 (7 pages).
Office Action dated Dec. 15, 2008 in U.S. Appl. No. 11/060,377 (8 pages).
Interview Summary dated Mar. 5, 2009 in U.S. Appl. No. 11/060,377 (2 pages).
Office Action dated May 27, 2009 in U.S. Appl. No. 11/060,377 (7 pages).
Extended European Search Report dated Jun. 28, 2016 for European Application No. 16156901.7 (7 pages).
Office Action dated Jan. 5, 2010 in U.S. Appl. No. 11/060,377 (10 pages).
Office Action dated Sep. 24, 2010 in U.S. Appl. No. 11/060,377 (7 pages).
A. Cameron, entitled "Basic Lubrication Theory", Ellis Horwood Limited, pp. 134-137, 1976.
A. Cameron, entitled "The Principles of Lubrication", John Wiley and Sons Inc., pp. 542-559, 1966.
Office Action dated May 12, 2010 in U.S. Appl. No. 10/980,425 (22 pages).
Philip E. Mitchell, Handbook Editor, "Tool and Manufacturing Engineers Handbook", 4th Edition, vol. VIII Plastic Part Manufacturing, Society of Manufacturing Engineers, Dearborn, Michigan, pp. 2-17 and 2-18, 1996 (4 pages).
U.S. Appl. No. 60/149,027, filed Aug. 16, 1999 with U.S. Patent & Trademark Office (44 pages).
U.S. Appl. No. 08/200,636, filed Feb. 23, 1994 with U.S. Patent & Trademark Office (40 pages).
Office Action dated Apr. 17, 1995 in U.S. Appl. No. 08/200,636 (4 pages).
Supplemental Information Disclosure Statement dated Sep. 11, 1995 in U.S. Appl. No. 08/200,636 (7 pages).
U.S. Appl. No. 08/437,781, filed May 9, 1995 with U.S. Patent & Trademark Office (84 pages).
Office Action dated Nov. 1, 1996 in U.S. Appl. No. 08/437,781 (2 pages).
U.S. Appl. No. 09/639,612, filed Aug. 15, 2000 with U.S. Patent & Trademark Office (67 pages).
International Search Report for PCT/US2009/053751 dated Oct. 14, 2009.
International Preliminary Report on Patentability dated Feb. 15, 2011 for PCT/US2009/053724 (9 pages).
International Preliminary Report on Patentability dated Feb. 15, 2011 for PCT/US2009/053735 (8 pages).
International Preliminary Report on Patentability dated Feb. 15, 2011 for PCT/US2009/053751 (7 pages).
International Preliminary Report on Patentability dated Feb. 15, 2011 for PCT/US2009/053762 (5 pages).
International Preliminary Report on Patentability dated Mar. 1, 2011 for PCT/US2009/055380 (9 pages).
International Preliminary Report on Patentability dated Mar. 1, 2011 for PCT/US2009/055397 (10 pages).
Photos 309 and 310 show a poster of which Applicant is aware. By disclosing these photos, Applicant is making no statement as to whether or not these photos are material or are prior art relative to the present application.
Communication from Canadian Intellectual Property Office dated Jan. 11, 2013 for Canadian patent application No. 2,735,235 (2 pages).
Supplementary European Search Report dated Apr. 22, 2013 for European Application No. 09 80 7307 (7 pages).
Communication dated Apr. 11, 2013 from Canadian Intellectual Property Office for Canadian patent application No. 2,735,236 (3 pages).
Communication dated May 22, 2013 from European Patent Office for European Patent Application No. 09807307.5-1506 (1 page).
Communication dated May 2, 2013 from European Patent Office for European Patent Application No. 09807307.5-1506, including Supplementary European Search Report and opinion (7 pages).
International Search Report dated Apr. 13, 2010 of International Searching Authority for Application No. PCT/US2009/055380 (2 pages).
International Search Report dated Oct. 13, 2009 of International Searching Authority for Application No. PCT/US2009/055397 (2 pages).
Office Action dated Oct. 9, 2007 in U.S. Appl. No. 10/980,425 (16 pages).
Office Action dated Apr. 7, 2008 in U.S. Appl. No. 10/980,425 (20 pages).
Office Action dated Jul. 17, 2008 in U.S. Appl. No. 10/980,425 (3 pages).
Office Action dated Oct. 29, 2008 in U.S. Appl. No. 11/325,530 (11 pages).
Office Action dated Jun. 26, 2009 in U.S. Appl. No. 11/325,530 (13 pages).
Office Action dated Oct. 19, 2009 in U.S. Appl. No. 11/325,530 (6 pages).
Dr. Nicole Rotter, J. Aigner, A. Naumann, H. Planck, C. Hammer, G. Burmester, M. Sittinger; abstract of article entitled "Cartilage Reconstruction in Head and Neck Surgery: Comparison of Resorbable Polymer Scaffolds for Tissue Engineering of Human Septal

(56) References Cited

OTHER PUBLICATIONS

Cartilage", in Journal of Biomedical Materials Research, vol. 42, issue 3, pp. 347-356, Dec. 5, 1998; accessed on Oct. 25, 2010 at http://onlinelibrary.wiley.com/doi/10.1002/(SICI)1097-4636(19981205)42:3%3C47::AID-JBM2%3E3.0.CO;2-J/abstract.
Robert J. Klebe; article entitled "Cytoscribing: A Method for Micropositioning Cells and the Construction of Two-and Three-Dimensional Synthetic Tissues", Experimental Cell Research 179 (1988) 362-373, published by Academic Presss, Inc.
Emanuel Sachs, Michael Cima, James Bredt, Alain Curodeau, Tailin Fan, and David Brancazio; article entitled "Cad-Casting: Direct Fabrication of Ceramic Shells and Cores by Three Dimensional Printing", Manufacturing Review vol. 5, No. 2, pp. 117-126, Jun. 1992, published by American Society of Mechanical Engineers.

\* cited by examiner

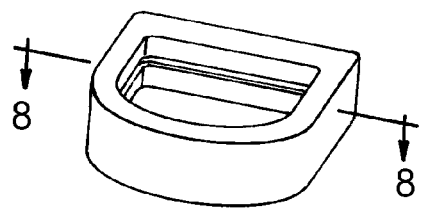
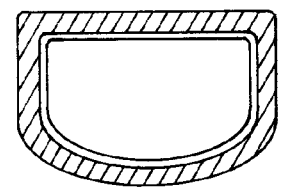
FIG. 7　　　　　　　　FIG. 8
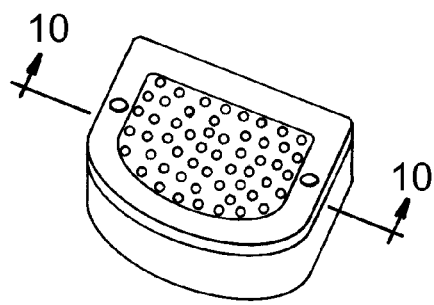
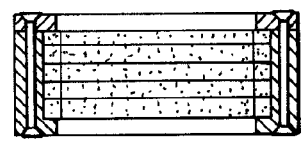
FIG. 9　　　　　　　　FIG. 10
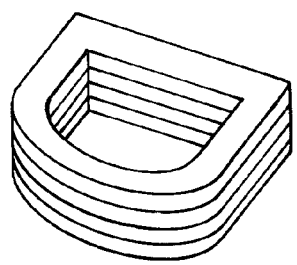
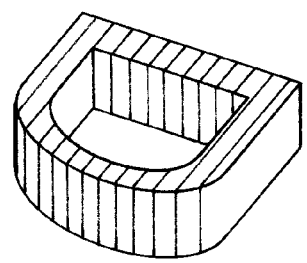
FIG. 11　　　　　　　FIG. 12

ORTHOPAEDIC IMPLANT WITH POROUS STRUCTURAL MEMBER

CROSS REFERENCE TO RELATED APPLICATIONS

This is a continuation-in-part application based upon U.S. patent application Ser. No. 12/540,515, entitled "ORTHOPAEDIC IMPLANT WITH POROUS STRUCTURAL MEMBER", filed Aug. 13, 2009, which is based upon U.S. provisional patent application Ser. No. 61/088,460, entitled "SPINAL DEVICES", filed Aug. 13, 2008, which is incorporated herein by reference.

BACKGROUND OF THE INVENTION

1. Field of the Invention

The present invention relates to orthopaedic devices, and, more particularly, to orthopaedic implants.

2. Description of the Related Art

Most orthopaedic implants are formed from a metallic material suitable for a given implant, such as a hip implant, knee implant, glenoid implant, etc. In the case of articulating joints, the implant may include a non-metallic load bearing surface, such as an ultra high molecular weight polyethylene (UHMWPE). The UHMWPE is attached to the metallic body of the implant, and provides the implant with good wear characteristics and low friction.

It is also known to provide an implant with a porous bony ingrowth surface. For example, a hip implant may include a porous surface on the stem which is intended to allow bony ingrowth of the proximal end of the femur bone. Such a porous surface may be in the form of a metal porous surface which is bonded, such as by heat sintering, to the stem of the implant. Examples of porous surfaces of this type include a woven mesh, a fiber mesh and particles. Knee implants are also known that include porous ingrowth surfaces that can bear load from surrounding anatomic structures.

Porous surfaces of the type described above which are used with implants are not typically part of a single structural member with two opposed, external porous surfaces. For example, in a knee implant, the distal surface of the implant can sit on the porous material that is slightly above the substrate material, but the porous material only typically has one external surface for tissue ingrowth. For hip implants, the porous ingrowth surface is usually provided as a coating on a structural component of the implant, such as the stem.

In some orthopaedic applications, such as spinal cages, it is beneficial to have a porous member that extends between two external, load bearing surfaces of the implant. In such arrangements, a cavity is typically formed between the two external surfaces of the implant and filled with a porous ingrowth material, which is typically a natural substance such as cancellous bone tissue. Such an implant is described in U.S. Patent Application No. 2002/0091447 to Shimp et al. One problem with the implant described by Shimp et al. is that harvesting sufficient cancellous bone tissue to fill the cavity is expensive, and host rejection issues can be a concern. Other similar implants that contemplate utilizing natural or synthetic materials are described in U.S. Patent Application Publication No. 2004/0210316 to King et al., and U.S. Pat. No. 6,423,095 to Van Hoeck et al. In each of these described implants, the porous material held in the cavity is fairly isolated from bearing load from surrounding anatomic structures after implantation, with external surfaces that are either flush or below the most protruding external surface of the main implant body. This is intentional, as the materials placed in the cavity tend to have significantly lower strength than the implant body. However, isolating the porous ingrowth material from bearing loads from surrounding anatomic structures also decreases the amount of surface area the porous ingrowth material has in contact with the anatomic structures, which can slow down integration of the implant. In addition, the porous materials placed in the cavity are typically resorbable by the body and will not last throughout the life of the implant.

What is needed in the art is an orthopaedic implant that can overcome some of the disadvantages of known devices.

SUMMARY OF THE INVENTION

The present invention provides an orthopaedic implant with a porous load bearing member held within a surface-to-surface cavity formed in the implant's body that projects outwardly away from an exterior surface of the implant.

The invention in one form is directed to an orthopaedic implant that includes an implant body having a first surface with a first peak, a second surface opposite the first surface, and a cavity formed therein that extends through the first surface and second surface. The implant body is substantially non-porous. A load bearing member comprising a substantially porous material is held within the cavity. The load bearing member has a first contact surface that extends out of the cavity past the first peak of the first surface.

The invention in another form is directed to an orthopaedic implant that includes an implant body having a first surface with a first peak, a second surface opposite the first surface, and a cavity formed therein that extends through the first surface and second surface. The implant body is substantially non-porous. A load bearing member comprising a substantially porous material is held within the cavity. The load bearing member has a first contact surface that extends out of the cavity and is proud of a portion of the first surface.

An advantage of the present invention is that the porous load bearing member can bear load from anatomic structures during implantation while providing a surface for tissue ingrowth.

Another advantage of the present invention is that an ingrowth material can be included on the implant to provide an additional surface for tissue ingrowth that has different ingrowth properties than the load bearing member.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 7 is a perspective view of an embodiment of a spinal cage with a ledge or groove;

FIG. 8 is a cross-sectional view of the spinal cage shown in FIG. 7 taken along line 8-8;

FIG. 9 is a perspective view of an embodiment of a spinal cage with a two-part solid component that is assembled to contain the porous material;

FIG. 10 is a cross-sectional view of the spinal cage shown in FIG. 9 taken along line 10-10;

FIG. 11 is a perspective view of an embodiment of a spinal cage with laminates perpendicular to an axis of the spinal cage;

FIG. 12 is a perspective view of an embodiment of a spinal cage with laminates parallel to an axis of the spinal cage;

The exemplifications set out herein illustrate embodiments of the invention, and such exemplifications are not to be construed as limiting the scope of the invention in any manner.

DETAILED DESCRIPTION OF THE INVENTION

I. Porous Spinal Devices—Laminate Designs

The present invention provides a laminate method for a spinal implant or implant component, including manufacturing methods for sheet creation, bonding/assembly methods, and ways of creating tapers. Further, the present invention provides delivery of therapeutic agents through a spinal device.

The present invention addresses these issues by providing the design and method of manufacturing of a porous spinal fusion device.

A. Materials

Material options for the spinal device include the following: implantable polymers (such as PEEK, PMMA), implantable reinforced polymers (such as carbon-fiber reinforced PEEK), implantable metals (such as titanium, titanium alloy), and implantable ceramics (such as hydroxyapatite, alumina). One or more of these materials can be combined in a given device.

B. Overall Design

Figure 1:
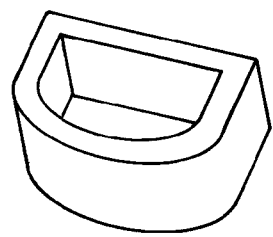
FIG. 1 is a perspective view of an embodiment of a solid component of a device formed according to the present invention.
Figure 2:
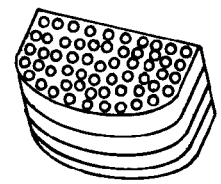
FIG. 2 is a perspective view of an embodiment of a porous component of a device formed according to the present invention.
Figure 3:
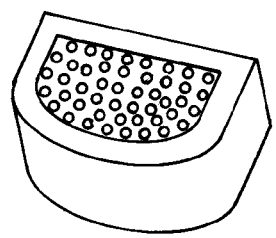
FIG. 3 is a perspective view of a device created from the solid component shown in FIG. 1 and the porous component shown in FIG. 2.

With regard to the overall design, the implant can include entirely porous material or one or more porous regions and one or more solid regions. Additionally, an entirely porous device can be created to mate with existing solid devices (See FIGS. 1-3).

The porous region is created by stacking layers of material with interconnecting holes/geometry (hereafter referred to as holes).

Figure 4:
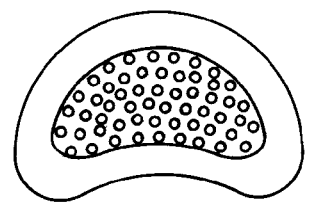
FIG. 4 is a cross-sectional view of a single, continuous layer with porous and solid regions.

The solid region can be formed by traditional techniques such as injection molding or machining or by bonding solid sheets together. The later method allows the solid and porous regions to be created from continuous sheets (See FIG. 4).

The holes in the sheets can be created by, for example, laser cutting, punching, etching, electrical discharge machining, plasma etching, electroforming, electron beam machining, water jet cutting, stamping, or machining. For polymer based materials, they can be created as the sheets are created by, for example, extruding, injection molding, or hot stamping.

Attachment of the sheets to each other can be achieved by any number of ways, including the following:

1. Heat. Heat can be generated by several ways:
   a. Ultrasonic welding—use ultrasonic waves to create heat at the interface of layers.
   b. Heat staking—use a heated tool to cause melting between the layers
   c. Vibratory welding
   d. Laser welding
   e. Convection—use an oven to create heat to cause bonding
   f. Intermediary layer—for example, use a material that can absorb energy waves that pass through the polymer (for example PEEK) without causing damage. The absorbed energy will cause localized heating. An example of such a coating is Clearweld by Gentex® Corporation. The laser waves that Clearweld absorbs pass through the PEEK without causing damage, allowing the layers to be melted together without large scale damage to the PEEK.

2. Chemical.
   a. Adhesives—a secondary material (such as adhesive) can be used to bond the material.
   b. Solvent bonding—a material in which the polymer or reinforced polymer is soluble can be applied to the sheet surfaces allowing multiple surfaces to be bonded to one another.
   c. Overmolding—overmolding of the polymer or reinforced polymer can provide a chemical bonding
3. Mechanical.
   a. Overmolding—overmolding of a polymer or reinforced polymer can create a mechanical lock between components on a micro or macro scale (microscale—the molded material locks with surface asperities of the existing material. Macroscale—features such as tongue-groove connections or undercuts). The overmolded material can be a separate component from the layers or one layer can be overmolded onto another layer.
   b. Features are provided within the layers or by a separate component which provides a mechanical lock—e.g. A pin, snap lock connection, dove-tail, tongue-groove, rivet, screw and/or melting tabs to create a mechanical lock. For example, one or more rivets can connect all layers of a porous implant together. These connection features can be made of any implantable material including, but not limited to, titanium, titanium alloy, PEEK, and/or other implantable polymers. These features can also be used as radiopaque markers as is described below.
   c. Some adhesives provide a mechanical bond in addition to or instead of a chemical bond.
4. Combinations of any/all of the above methods.

If the porous and solid regions are created separately (as in FIGS. 1-3), it may be desirable to bond the two together. There are several methods of achieving this bond:

1. Heat. Heat can be generated by several ways:
   a. Ultrasonic welding—use ultrasonic waves to create heat at the interface of layers.
   b. Heat staking—use a heated tool to cause melting between the layers
   c. Vibratory welding
   d. Laser welding
   e. Convection—use an oven to create heat to cause bonding
   f. Intermediary layer—for example, use a material that can absorb energy waves that pass through the polymer (for example PEEK) without causing damage. The absorbed energy will cause localized heating. An example of such a coating is Clearweld by Gentex® Corporation. The laser waves that Clearweld absorbs pass through the PEEK without causing damage, allowing the layers to be melted together without large scale damage to the PEEK.
2. Chemical.
   a. Adhesives—a secondary material (such as adhesive) can be used to bond the material.
   b. Solvent bonding—a material in which the polymer or reinforced polymer is soluble can be applied to the sheet surfaces allowing multiple surfaces to be bonded to one another.
   c. Overmolding—overmolding of the polymer or reinforced polymer can provide a chemical bonding
3. Mechanical.
   a. Overmolding—overmolding of a polymer or reinforced polymer can create a mechanical lock between components on a micro or macro scale (microscale—the molded material locks with surface asperities of the existing material. Macroscale—features such as tongue-groove connections or undercuts). The overmolded material can be a separate component from the layers or one layer can be overmolded onto another layer.
   b. Features are provided within the layers or by a separate component which provides a mechanical lock—e.g. A pin, snap lock connection, dove-tail, tongue-groove, rivet, and/or melting tabs to create a mechanical lock. For example, the porous material can attach to the windows that are typical in spinal cages or to a groove or ledge is created along the interior edge of the solid ring (see FIGS. 5-10). These connection features can be made of any implantable material including, but not limited to, titanium, titanium alloy, PEEK, and/or other implantable polymers. These features can also be used as radiopaque markers as is discussed later in this disclosure.
   c. Some adhesives provide a mechanical bond in addition to or instead of a chemical bond.
4. Combinations of any/all of the above methods.

Assembly of layer to layer or one component to another (for example a porous component to a solid component) can be aided by such ways as surface modifications to improve adhesive or solvent bonding or roughened surfaces.

Figure 5:
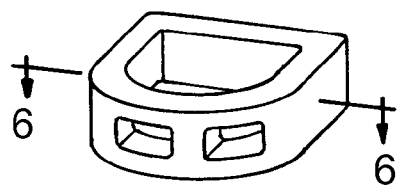
FIG. 5 is a perspective view of an embodiment of a spinal cage with windows.
Figure 6:
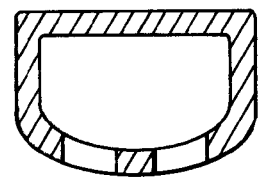
FIG. 6 is a cross-sectional view of the spinal cage shown in FIG. 5 taken along line 6-6.

FIGS. 5-6 illustrate a spinal cage showing windows (a cross section view is shown at the right). This is an example of a type of feature onto which the porous component can be bonded.

FIGS. 7-8 illustrate a spinal cage showing a ledge or groove (a cross section view is shown at the right). This is an example of a type of feature onto which the porous component can be bonded.

FIGS. 9-10 illustrate a spinal cage showing a two-part solid component that is assembled to contain the porous material. In this example mechanical means (screw/rivet) are used in conjunction with an adhesive bond. Adhesive ways alone, mechanical ways alone or any of the other manufacturing methods discussed in this disclosure are also options.

Figure 13:
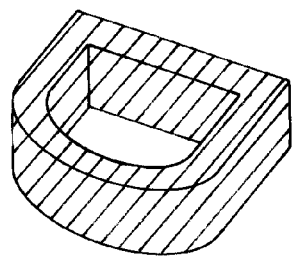
FIG. 13 is a perspective view of an embodiment of a spinal cage with laminates at an angle to an axis of the spinal cage.
Figure 14:
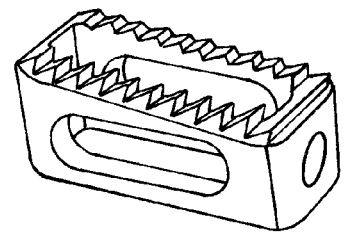
FIG. 14 is a perspective view of an embodiment of a spinal cage.
Figure 15:
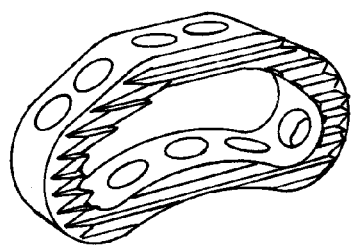
FIG. 15 is a perspective view of another embodiment of a spinal cage.
Figure 16:
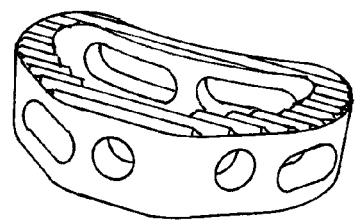
FIG. 16 is a perspective view of yet another embodiment of a spinal cage.
Figure 17:
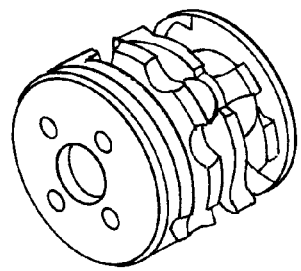
FIG. 17 is a perspective view of yet another embodiment of a spinal cage.

FIGS. 11-13 illustrate a spinal cages showing laminates perpendicular, parallel, and at an angle to the axis of the implant.

The laminate portion of the implant can have layers oriented in any direction. For example, the layers can be perpendicular, parallel, or at an angle to the axis of the implant (See FIGS. 11-13). This angle need not be constant within an implant.

The overall shape of the implant can be of any typical existing type, such as ALIF, TLIF, PLIF, and standard round cages (see FIGS. 14-17)

C. Delivery of Therapeutic Agent.

Figure 18:
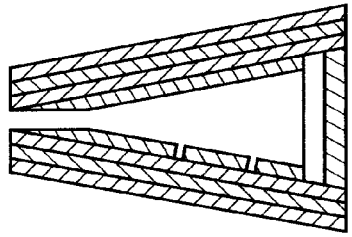
FIG. 18 is a sectional view of an implant with features for the delivery of therapeutic agents.

This device can be used to deliver therapeutic agents directly to the tissue surrounding the implant (See FIG. 18). Some examples of situations in which this would be desired: delivery of oncology treatments to cancerous tissue or tissue surrounding cancerous tissue; delivery of agents (such as BMP, hydroxyapatite slurry, and/or platelets) to encourage/enhance bone growth to promote faster and better fusion; and delivery of analgesic agents to reduce pain. This list is not exhaustive.

FIG. 18 illustrates a sectioned, side-view of an implant with features for the delivery of therapeutic agents.

The implant can include a reservoir for delivery of the therapeutic agent over an extended period of time. Openings leading from the reservoir to the porous material allow for controlled release of the therapeutic agents at a desired rate. The reservoir can be refilled at any time before, during, or after the surgery.

If immediate delivery of the therapeutic agents to the surrounding tissue is all that is required (not extended time release), the design need not include a reservoir. In this case, the therapeutic agents can be directly routed from the implant access to the porous material via channels. However, a reservoir can be included in an immediate delivery design; the openings in the reservoir would be sized to allow for immediate release of the therapeutic agent rather than a slower, long-term delivery.

The access in the implant (see FIG. 18) can mate with an insertion of a delivery tool (such as a needle) or a device (or catheter leading to a device) to allow for remote filling of the reservoir (such as by way of a subcutaneous port or external pain-pump).

In order to allow and promote bone growth through the implant from one vertebra to the other, openings run from the superior to the inferior portion of the implant and be appropriately sized to allow for bone ingrowth (See FIG. 18).

D. Anterior-Posterior Taper

Figure 19:
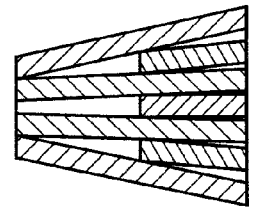
FIG. 19 is a sectional view of a tapered implant.
Figure 20:
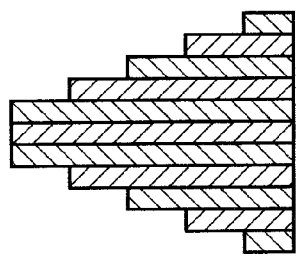
FIG. 20 is a sectional view of another tapered implant.
Figure 21:
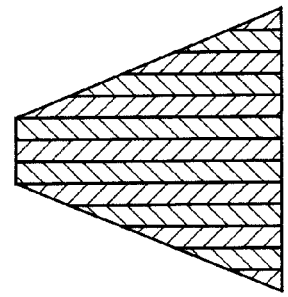
FIG. 21 is a sectional view of yet another tapered implant.
Figure 22:
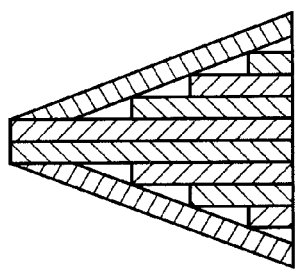
FIG. 22 is a sectional view of yet another tapered implant.
Figure 23:
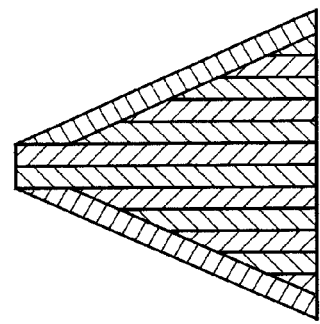
FIG. 23 is a sectional view of yet another tapered implant.

Some implants are tapered to mate with the natural anterior-posterior taper that exists between vertebrae. If a solid portion exists, this taper can be created by traditional machining and/or molding techniques. In the porous region, there are several ways of creating this taper, including the following:

a. If the design includes a reservoir, the reservoir itself can be tapered. The porous ingrowth layers can be of uniform thickness and layered outside of the reservoir (as indicated in FIG. 18).
b. A wedge-shaped piece or pieces can create the taper with the ingrowth layers stacked on the wedge(s). This is essentially the same design as shown in FIG. 20 without the reservoir, access and holes for the therapeutic agent delivery. To allow and promote bone growth through the implant from one vertebra to the other, openings run from the superior to the inferior portion of the implant and be appropriately sized to allow for bone ingrowth (See FIG. 18).
c. Shorter layers can be stacked with larger layers to create an overall taper as in FIG. 19.
d. Layers of varying lengths can be sacked to create a stepped taper as in FIG. 20.
e. Similar to the technique in (d), layers of varying length can be stacked. A smooth taper can be created by using layers that are tapered prior to stacking or the smooth taper can be created, by such ways as machining or hot forming, after the layers are stacked. The second of these would involve first creating a part like that in (d), then removing material to create the smooth taper shown in FIG. 21.
f. Another way of creating a smooth surface on a stepped taper is to have one or more outer layers which are parallel to the taper face, as shown in FIG. 22.
g. The design in (f) does not allow for a large amount of contact area between the outer layer of the taper and the corners of the stepped layer. One way of providing increased contact area (which can provide increased strength) is to taper the stepped layers as in FIG. 21 before adding the outer layer(s) that are parallel to the face of the taper. An example of this is shown in FIG. 23.

E. Interface with Bone

It is often desirable to have an implant-bone interface with relative high friction. Traditionally, this is achieved by such ways as a roughened implant surface, teeth (See FIGS. 24-25), spikes, or hooks.

In a laminate implant, there are several options for creating such features. These options include the following:

a. Form features prior to bonding laminate sheets: Form teeth or other "rough" features into the outermost layers of the implant prior to bonding them to the other sheets. These teeth can be created by several ways:
   i. Form material—for example: heat forming, cold forming.
   ii. Remove material—for example: machining, laser cutting, chemical etching.
   iii. Add material—attach material to create the features by, for example, insert molding, mechanical attachment, adhesive bonding, laser welding, solvent bonding.
b. Form features after bonding laminate sheets: Form the rough surface features on the faces of the implant after the sheets have been bonded. These features can be formed by the same ways as listed in (a).
c. Secondary feature (such as hooks, spikes, etc) protruding from the implant into the bone. This feature can be attached by, for example, insert molding, mechanical attachment, adhesive bonding, laser welding, or solvent bonding.

Figure 24:
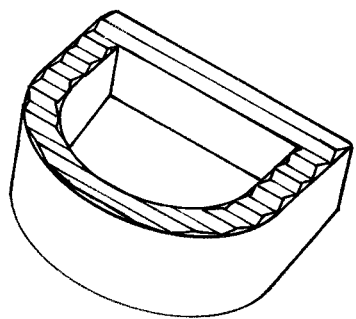
FIG. 24 is a perspective view of an implant showing teeth that mate with surrounding bone.
Figure 25:
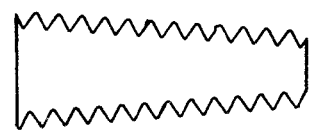
FIG. 25 is a side view of the implant shown in FIG. 24.

FIGS. 24-25 illustrate an implant showing teeth that mate with the surrounding bone.

F. Interface with Instruments

To aid in insertion of the implant into position in the body, it is often necessary to attach the implant to instrumentation. The material near the interface of the instrument and implant can often see additional stress. In a partially or fully laminate implant, it may be necessary to provide additional support in the region of this interface. This can be achieved by a number of ways, including: designing the instrument to reduce stresses and/or strengthening the implant in the region of the interface. For example, in the case of an instrument that contains a male thread which mates with a female thread in the implant, the implant can be strengthened by adding metal, solid polymer, or reinforced polymer in the region of the female thread. In machine design, thread inserts are frequently used to repair damaged threads. In this case, thread inserts can be used to strengthen the implant at the interface with the instrument(s).

G. Radiopaque Markers

When a radiolucent material, such as unfilled PEEK, is used, it is sometimes desirable to have the ability to see some or all of that implant on a diagnostic tool such as x-ray without the white-out problems of solid metal. For example, the surgeon may use such markers to determine the orientation and position of the implant to ensure proper placement during surgery. Radiopaque markers can provide this ability. The opacity and/or amount of radiopaque material can be controlled so that the marker does not prevent evaluation of the tissue near the implant by x-ray or other diagnostic ways. Material options include, but are not limited to, the following:

a. Implantable metals (stainless steel, titanium, or titanium alloys for example).
b. Barium sulfate filled PEEK.
c. Carbon filled PEEK.
d. Other polymers with radiopaque material (such as barium sulfate or zirconium dioxide).

Examples of the marker design include one or more of the following:
  a. One or more radiopaque pins.
  b. Assembly features such as rivets or pins.
  c. Coating a portion of the device with a radiopaque material. Examples of methods for creating a radiopaque coating include, but are not limited to, the following:
    i. Using chemical vapor deposition to deposit a layer of titanium onto the polymer.
    ii. Using a radiopaque ink such as Radiopaque™ ink (developed by CI Medical).
  d. One or more of the laminate layers being radiopaque. Examples of methods to make the layer(s) radiopaque include, but are not limited to, the following:
    i. Making the layer from an implantable metal (such as tantalum, titanium, titanium alloy, cobalt chrome, or stainless steel).
    ii. Using a barium sulfate filled polymer to create the layer.
    iii. Coating the layer with a radiopaque material—for example, using chemical vapor deposition to deposit a layer of titanium onto the surface of one or more layers.
  e. A slightly radiopaque porous material. This can be achieved, for example, by using a polymer with barium sulfate.

II. Porous Polymer Spinal Fusion Devices

The key to the success of a spinal fusion surgery is the formation of good bone growth between the vertebrae that are being fused. Evaluation of this bone growth is, thus, critical to determining the progress and eventual success of the surgery.

Existing porous spinal cages are made of biocompatible metals. Due to the density of these metals, the implants made post-operative examination of the tissue surrounding the implant difficult.

Several current devices are now made from solid biocompatible polymers such as PEEK. PEEK is a relatively radiolucent material. While this addresses the issue of radiopacity for solid fusion devices, it is often desired to encourage more rapid bone growth between the two vertebrae.

One solution for this problem is implants made from porous biocompatible polymers, such as PEEK or reinforced porous PEEK.

A. Overall Design

Such implants can be entirely porous or have a mix of porous and solid polymer. For example, a solid ring of material can surround a porous core (See FIG. 26).

Figure 26:
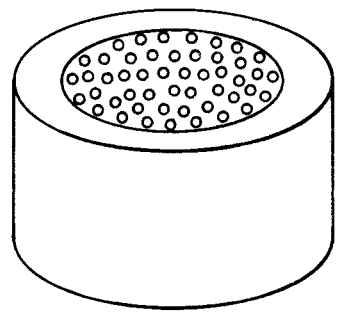
FIG. 26 is a spinal fusion device.

FIG. 26 illustrates a spinal fusion device with solid region (Region 1) and porous region (Region 2)

One embodiment of the design is a porous center component that mates with existing solid, ring-like devices. This device could be assembled with the solid device in a manufacturing setting or in the operating room.

If a solid region/component exists, the porous and solid regions may need, but do not necessarily need, to be attached to one another. Examples of methods that can be used to attach the porous and solid material are:
  a. Mechanical features—snap-fit connections, 'dove-tail' types of connections.
  b. Adhesive bonding.
  c. Solvent bonding.
  d. Heat applied by, for example, laser, ultrasonic or vibratory welding, convection heating, heat staking B. Material
  a. Method of creating porosity
    i. Laminate design—bonding sheets of material which contain holes.
    ii. Foaming methods.
    iii. Bond 'beads' of polymer—bead of any shape can be bonded together (via, for example, heating, adhesive bonding, or solvent bonding) to create a porous structure.
    iv. Mix of polymer and dissolvable material.
      1. One method involves creating a mixture of powdered implantable material (e.g. PEEK) and a powder (e.g. salt) that is soluble in something in which the implantable material is not soluble (such as water, isopropyl alcohol for the PEEK example). The mixture is then heated to bond the implantable particles together. Pressure can also be applied to aid in the bonding of particle to particle. Heat can be created by convection or other ways (such as coating the powder with a material that absorbs a given range of energy waves—such as laser waves—and causes heating. E.g. Clearweld coating by Gentex® Corporation). Finally, dissolve away the filler to create the porous implantable material. This method can create net shape parts or raw material shapes from which individual parts can be created.
      2. Another method involves mixing an implantable polymer with a dissolvable material such as described above. The mixture is then pelletized and then injection molded to an intermediary or the final part shape. The filler is dissolved away to create the porous implantable polymer.
  b. Reinforcement—If improved mechanical properties are desired, various reinforcing materials can be used. For example, carbon fiber or barium sulfate can be used.

C. Radiopaque Markers

It is sometimes desirable to have the ability to see some of the implant on a diagnostic tool such as an x-ray without the white-out problems of solid metal. For example, the surgeon may use such markers to determine the orientation and position of the implant to ensure proper placement during surgery. Radiopaque markers can provide this ability. The opacity and/or amount of radiopaque material can be controlled so that the marker does not prevent evaluation of the tissue near the implant by x-ray or other diagnostic ways. Material options include, but are not limited to, the following:
  a. Implantable metals (stainless steel, titanium, or titanium alloys for example).
  b. Barium sulfate filled PEEK.
  c. Carbon filled PEEK.
  d. Other polymers with radiopaque material (such as barium sulfate or zirconium dioxide).

Examples of the marker design include one or more of the following:
  a. One or more radiopaque pins.
  b. Coating a portion of the device with a radiopaque material. Examples of methods for creating a radiopaque coating include, but are not limited to, the following:
    i. Using chemical vapor deposition to deposit a layer of titanium onto the polymer.
    ii. Using a radiopaque ink such as Radiopaque™ ink (developed by CI Medical).

c. A slightly radiopaque porous material. This can be achieved, for example, by using a polymer with barium sulfate.

Figure 27:
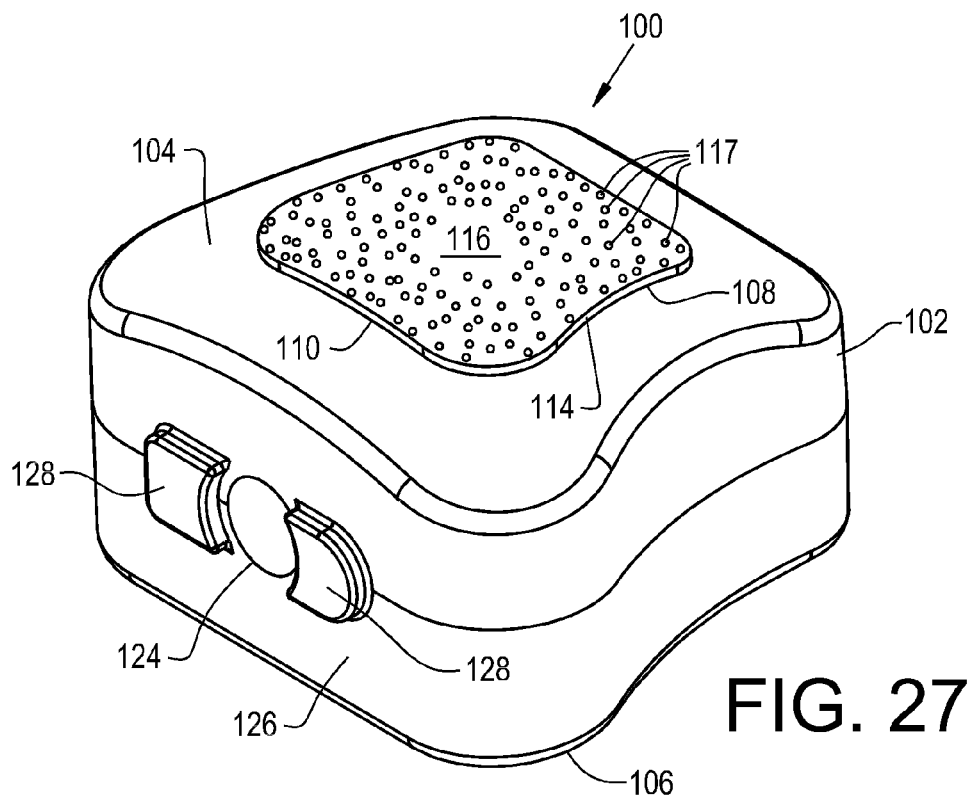
FIG. 27 is a perspective view of another embodiment of an orthopaedic implant according to the present invention.
Figure 28:
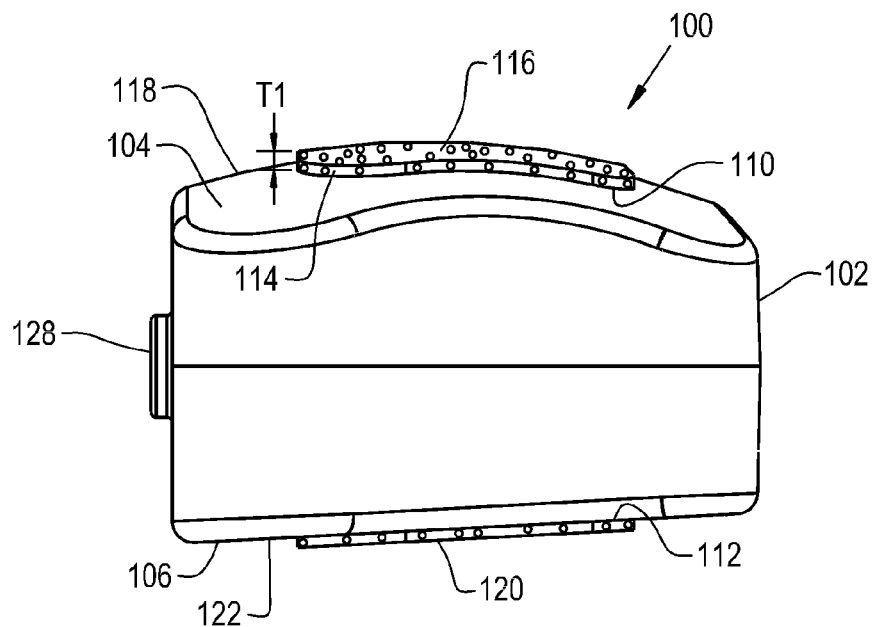
FIG. 28 is a side view of the orthopaedic implant shown in FIG. 27.
Figure 29:
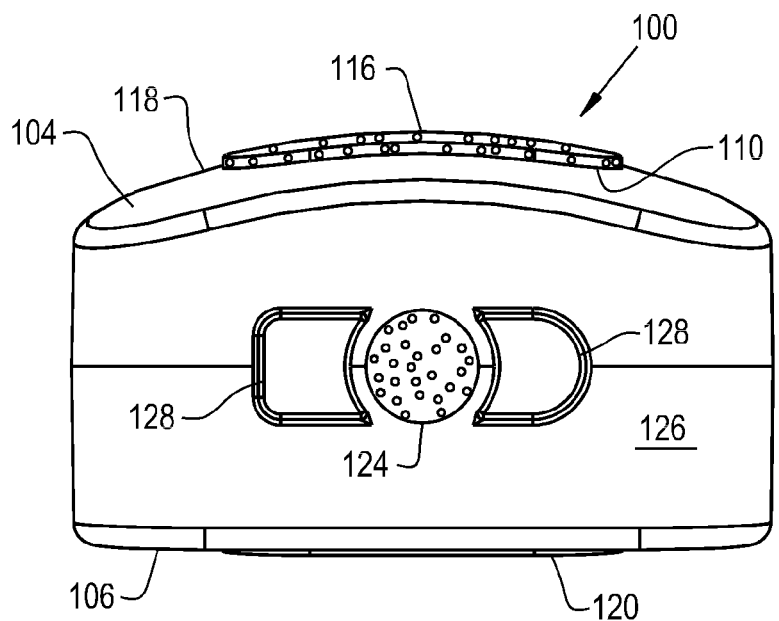
FIG. 29 is a front view of the orthopaedic implant shown in FIGS. 27-28.

Referring now to FIGS. 27-29, an embodiment of an orthopaedic implant 100 according to the present invention is shown that includes an implant body 102 formed from a substantially non-porous material having a first surface 104 and a second surface 106 opposite the first surface 104. As used herein, "substantially non-porous" indicates a porosity of 5% or less, so that the implant body 102 is mostly solid. The implant body 102 can be formed from a variety of different materials that are biocompatible and commonly used to form orthopaedic implants, including polyether ether ketone (PEEK), other polyaryl ether ketones (PAEKs), titanium, stainless steel, cobalt chrome, ultra-high molecular weight polyethylene (UHMWPE), or any previously described material. It should be appreciated that these materials are exemplary only and other biocompatible materials could be used to form the implant body. As shown in FIGS. 27-29, the implant body 102 is formed in the shape of a cervical cage for spinal applications, but other shapes can also be used, as shown further herein. The first surface 104 and second surface 106 can be curved, as shown, or can be formed as planar surfaces that are substantially flat. Alternatively, one of the surfaces 104, 106 can be formed as a surface with one or more curvatures while the other surface is planar.

A cavity 108 is formed in the implant body 102 extending through the first surface 104 and second surface 106 to form a continuous cavity 108 through the implant body 102. The cavity 108 has a first cavity entrance 110 formed through the first surface 104 and a second cavity entrance 112 (shown in FIG. 28) formed through the second surface 106. One or both of the cavity entrances 110, 112 can be concentrically formed through their respective surface 104, 106 so that the cavity entrances 110, 112 have a perimeter shape that approximately matches a perimeter shape of their respective surface 104, 106, with the cavity entrances 110, 112 having a smaller perimeter than their respective surfaces 104, 106. The cavity 108 can be formed to have a constant or varying shape throughout.

A load bearing member 114 comprising a substantially porous material having a first contact surface 116 is held within the cavity 108 that is formed within the implant body 102. As used herein, "substantially porous" indicates a porosity of at least 20%, but can be significantly higher. For example, the load bearing member 114 can have a total volume, that is the entire volume occupied by the load bearing member 114, of which 60% or more is defined by pores 117 formed in the load bearing member 114. In other words, 40% of the total volume of the load bearing member 114 can be occupied by structural material forming the load bearing member 114 while 60% of the total volume is occupied by empty spaced defined by the pores 117, in aggregate. If an extremely porous material is used to form the load bearing member 114, the pores 117, in aggregate, can occupy 80% or more of the total volume of the load bearing member 114. If desired, one or more therapeutic agents can be held within some or all of the pores 117 for elution into surrounding anatomic features after implantation of the orthopaedic implant 100 to increase the efficacy of the surgical procedure. A non-exhaustive list of possible therapeutic agents that can be provided in the pores 117 includes various growth factors, bone morphogenetic factors, bone morphogenetic proteins, anti-microbial agents, anti-inflammatories, anti-coagulants, painkillers, cytotoxic substances, stem cells, and any other substance, known or unknown, that is desirable to elute from the orthopaedic implant 100 following implantation. The material(s) used to form the load bearing member 114 should, like the implant body 102, be biocompatible so that the orthopaedic implant 100 is suitable for implantation at an anatomical site within a patient. It is also useful if the load bearing member 114 is formed from one or more materials that are non-resorbable, i.e., the material of the load bearing member 114 can maintain at least 90% of its original mass after being implanted in a living patient for at least a year. Examples of such materials are PEEK, tantalum, and titanium, but other porous materials are also contemplated as being used. The load bearing member 114 can comprise either a synthetic material, such as those previously described, or one or more naturally derived materials, such as a bone graft. The naturally derived material can also be, for example, cells or tissues harvested from the patient or a different organism, scaffolds created using collagen or other biomaterials, etc. It is useful, but not required, for the load bearing member 114 to substantially fill the cavity 108 so that at least 90% of the empty space in the implant body 102 defined by the cavity 108 is filled by the bearing member 114. Such filling of the cavity 108 by the load bearing member 114 makes it easier to hold the load bearing member 114 within the cavity 108 during implantation.

The first surface 104 defines a first peak 118, which is a point on the first surface 104 that has a maximum height, relative to a ground surface, when the second surface 106 of the implant body 102 is laid on the ground surface. The first peak 118 of implant body 102 is best shown in FIG. 28, where it can be seen that the first peak 118 is adjacent to the first cavity entrance 110. With further reference to FIG. 28, it can be seen that the first contact surface 116 of the load bearing member 114 extends out of the cavity 108 past the first cavity entrance 110 so that the first contact surface 116 extends past the first peak 118, i.e., the first contact surface 116 is proud of the first surface 104. In this sense, the first contact surface 116 defines a thickness T1 that extends past and projects from the first surface 104, which can be either constant or varying throughout the first contact surface 116. By extending the first contact surface 116 past the first peak 118 of the first surface 104, the first contact surface 116 can be placed in contact with an anatomic structure, such as a vertebrae, during implantation while isolating the first surface 104 from contact with the anatomic structure. Once implanted, the porous load bearing member 114 can then bear load from the anatomic structure while allowing for ingrowth of tissue into the load bearing member 114 through the pores 117.

Due to the varying shapes of anatomic structures and desired load bearing characteristics, the first contact surface 116 can be a curved surface or a planar surface. The relative sizing between the first surface 104 and the first contact surface 116 can also be adjusted, as desired, to balance the load bearing characteristics of the load bearing member 114. As can be seen, the first contact surface 116 defines a contact surface area and the first surface 104 defines a first surface area, with the contact surface area and first surface area together defining a top surface area of the orthopaedic implant 100. The relative percentage of the top surface area that the contact surface area makes up can be altered to give varying amount of contact surface for anatomic structures during implantation. It is contemplated that the contact surface area can be 40 to 90% of the total surface area when a large contact surface 116 is desired, or less than 40% of the total surface area when a smaller contact surface 116 is desired. It should be understood that the term "top surface area" is used for convenience of description only and not to limit the scope of the present invention.

Optionally, the load bearing member 114 can have a second contact surface 120 extending out of the cavity 108 past the second cavity entrance 112 so that it extends past a second peak 122 of the second surface 106 of the implant body 102. The second peak 122 of the second surface 106 is analogous to the first peak 118 of the first surface 104, with the key difference being that the second peak 122 defines a maximum height of the second surface 106 relative to a ground surface when the first surface 104 is laid on the ground surface. The second contact surface 120 can be configured and altered similarly to the first contact surface 116 so that the second contact surface 120 can be in contact with an anatomic structure following implantation. The second contact surface 120 can be a mirror image of the first contact surface 116 or a different configuration, depending on the desired load bearing characteristics of the load bearing member 114 caused by loads bearing on the first and second contact surfaces 116, 120 from surrounding anatomic structures. It can be useful if the pores 117 of the load bearing member 114 interconnect from the first contact surface 116 to the second contact surface 120 so that a travel path through the entirety of the load bearing member 114 can be formed through interconnected pores 117 formed therein.

To assist in implanting the orthopaedic implant 100, an opening 124 can be formed through another surface 126 of the implant body 102 to the cavity 108. The opening 124 can be any size or shape that allows for an insertion tool (not shown) to be placed within the opening 124 to help steady and position the orthopaedic implant 100 during implantation. The load bearing member 114 can partially extend into the opening 124, another material can be held in the opening 124, or the opening 124 can provide a clear path to the load bearing member 114 held in the cavity 108. In a similar manner, one or more protrusions 128 can be placed adjacent to the opening 124 that are shaped to interact with the insertion tool and provide a more stable connection between the orthopaedic implant 100 and the insertion tool. The opening 124 and protrusion(s) 128 can also be configured so that a removal tool (not shown), rather than an insertion tool, can interact with the opening 124 and protrusion(s) 128 to remove the orthopaedic implant 100 from a patient following implantation, if necessary.

Figure 30:
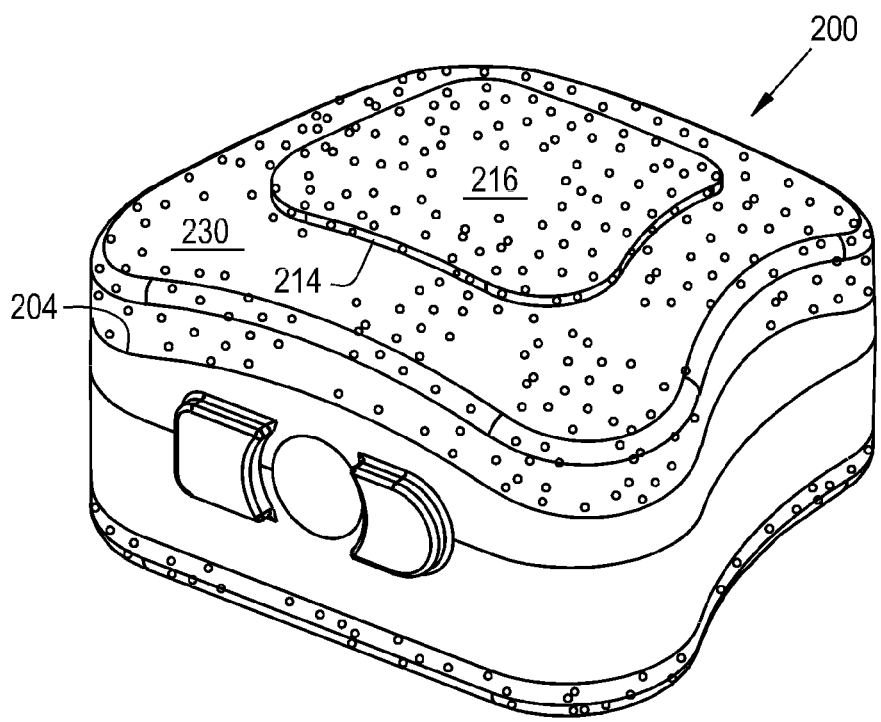
FIG. 30 is a perspective view of yet another embodiment of an orthopaedic implant according to the present invention.
Figure 31:
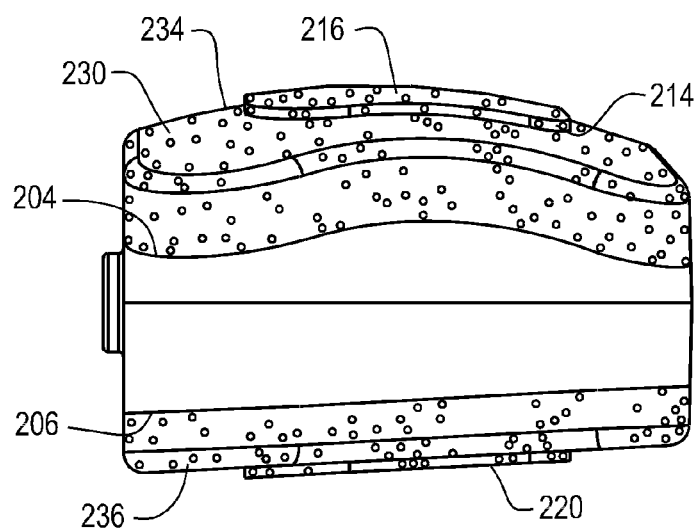
FIG. 31 is a side view of the orthopaedic implant shown in FIG. 30.

Referring now to FIGS. 30-31, another embodiment of an orthopaedic implant 200 is shown that is configured similarly to orthopaedic implant 100 previously described. For brevity of description, all features of orthopaedic implant 200 that are analogous to features of orthopaedic implant 100 are numbered similarly but raised by 100. As can be seen, the first surface 204 of the implant body 202 is covered by an ingrowth material 230, shown as a porous endplate. The ingrowth material 230 can cover all or part of the first surface 204 to encourage ingrowth of surrounding tissues into the ingrowth material 230 following implantation and provide good integration of the orthopaedic implant 200. The ingrowth material 230 can be formed of any material that encourages ingrowth of a desired body tissue into the ingrowth material 230. A non-exhaustive list of contemplated materials includes porous titanium, tantalum, hydroxyapatite, tricalcium phosphate, PEEK, PAEK, polymethyl methacrylate (PMMA), polylactic acid (PLA), and polyglycolic acid (PGA), but it should be understood that many other types of materials can be used as the ingrowth material 230. Since the load bearing member 214 will initially bear the brunt of the load from surrounding anatomic structures, the ingrowth material 230 can be formed of a lower strength material, with a higher porosity than the load bearing member 214, or both. For example, the load bearing member 214 can be formed of a reinforced PEEK material that has a porosity of 60% and the ingrowth material 230 can be formed of a PEEK material that has a porosity of 80%. This allows for orthopaedic implant 200 to have a higher strength material of the load bearing member 214 initially bear the brunt of the load from surrounding anatomic structures while a higher porosity material of the ingrowth material 230 allows for better tissue ingrowth to fixate the orthopaedic implant 200.

As shown in FIG. 31, the ingrowth material 230 has an ingrowth peak 234, which is the highest point of the ingrowth material 230 relative to a ground surface when the implant body 202 rests its second surface 206 on the ground surface. The first contact surface 216 of the load bearing member 214 extends out of the cavity 208 formed in the implant body 202 past the ingrowth peak 234, so that the first contact surface 216 can bear load from an anatomic structure following implantation and isolate the ingrowth material 230 from initially bearing load from the anatomic structure. The orthopaedic implant 200 can have a second ingrowth material 236 covering all or part of the second surface 206 of the implant body 202 and the load bearing member 214 can have a second contact surface 220 extending past the second ingrowth material 236 similarly to how the first ingrowth material 230 extends past the ingrowth peak 234 of the ingrowth material 230. In this sense, the ingrowth materials 230, 236 have surfaces that are analogous to the first and second surfaces 104, 106 of orthopaedic implant 100 and which the load bearing member 214 extends past.

Figure 32:
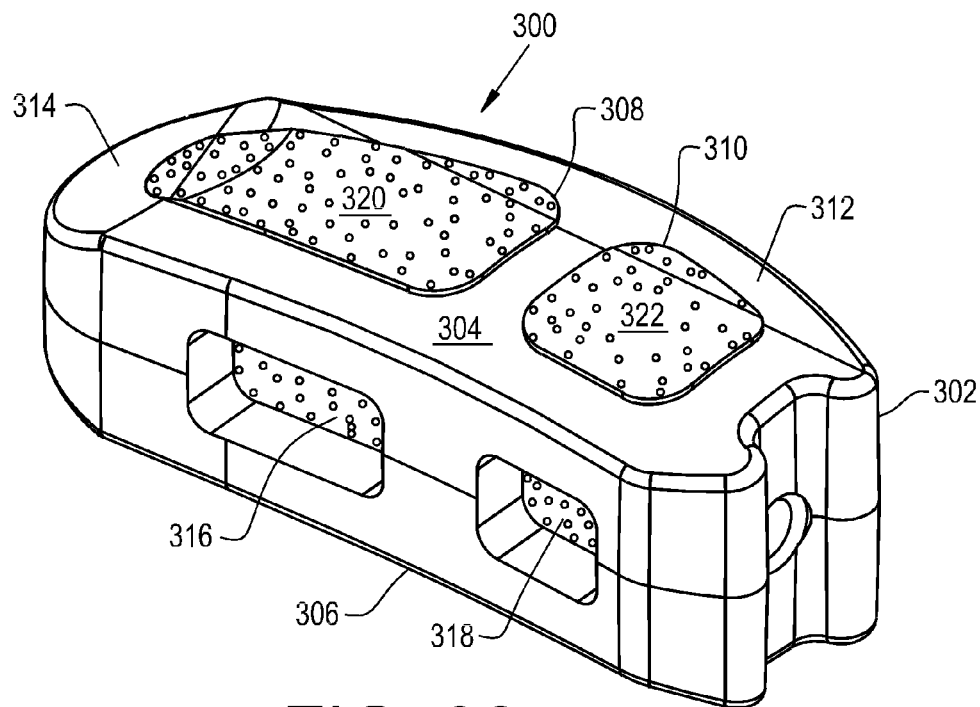
FIG. 32 is a perspective view of yet another embodiment of an orthopaedic implant according to the present invention.
Figure 33:
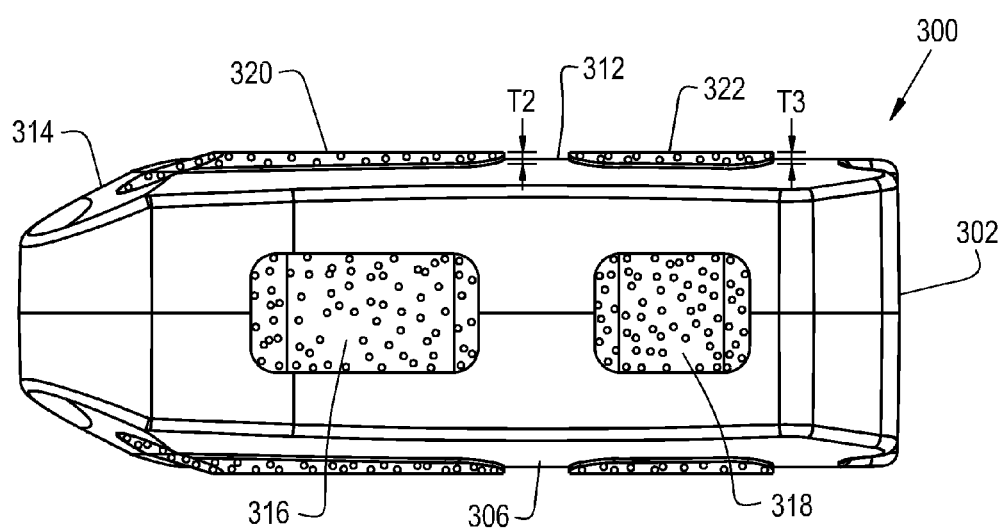
FIG. 33 is a front view of the orthopaedic implant shown in FIG. 32.
Figure 34:
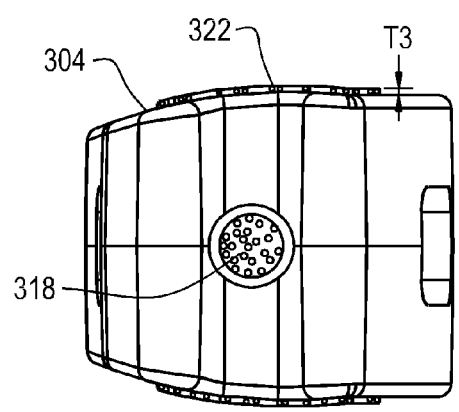
FIG. 34 is a side view of the orthopaedic implant shown in FIGS. 32-33.

Referring now to FIGS. 32-34, another embodiment of an orthopaedic implant 300 according to the present invention is shown that includes an implant body 302 configured to be used as a lumbar cage. The implant body 302 is comprised of a substantially non-porous material and has a first surface 304; a second surface 306 opposite the first surface 304; a first cavity 308 formed through the first surface 304 and second surface 306; and a second cavity 310 formed through the first surface 304 and second surface 306. As can be seen, the implant body 302 has a planar portion 312 that is flat and a curved portion 314 that has a sloped curvature. The cavities 308, 310 can be formed through the first and second surface 304, 306 all or partially within either the planar portion 312 or curved portion 314. A first load bearing member 316 is held within the first cavity 308 and a second load bearing member 318 is held within the second cavity 310. The first load bearing member 316 has a first contact surface 320 and the second load bearing member 318 has a third contact surface 322 that each extend out of their respective cavity 308, 310 past the plane of the planar portion 312, so that the contact surfaces 320, 322 can bear load from surrounding anatomic features following implantation. The load bearing members 316, 318 and their contact surfaces 320, 322 can be configured similarly to previously described load bearing members 114, 214, and even though the load bearing members 316, 318 are shown as having different sizes and total volumes, their size and total volume could be equal. The contact surfaces 320, 322 each define a respective thickness T2, T3 relative to the planar portion 312 of the first surface 304. The thicknesses T2, T3 of the contact surfaces 320, 322 can be equal to each other or could be different to provide different load bearing characteristics. For example, it may be desirable to provide load bearing member 316 with a thicker contact surface 320 than the contact surface 322 of load bearing member 318 due to the larger overall volume of load bearing member 316, in which case T2 would be greater than T3. It is also contemplated that the load bearing members 316 and 318 can be formed of different materials, have differing porosities, or be otherwise configured differently from one another to produce a desired healing effect.

Figure 35:
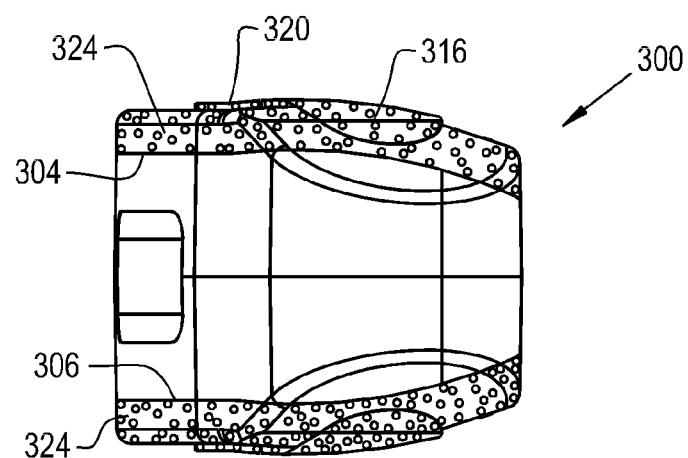
FIG. 35 is a side view of the orthopaedic implant shown in FIGS. 32-34 including an ingrowth material.

Referring now to FIG. 35, the orthopaedic implant 300 shown in FIGS. 32-34 is shown with ingrowth material 324 covering the first and second surfaces 304, 306 of the implant body 302. The ingrowth material 324 can be configured in an analogous manner to previously described ingrowth material 230.

Figure 36:
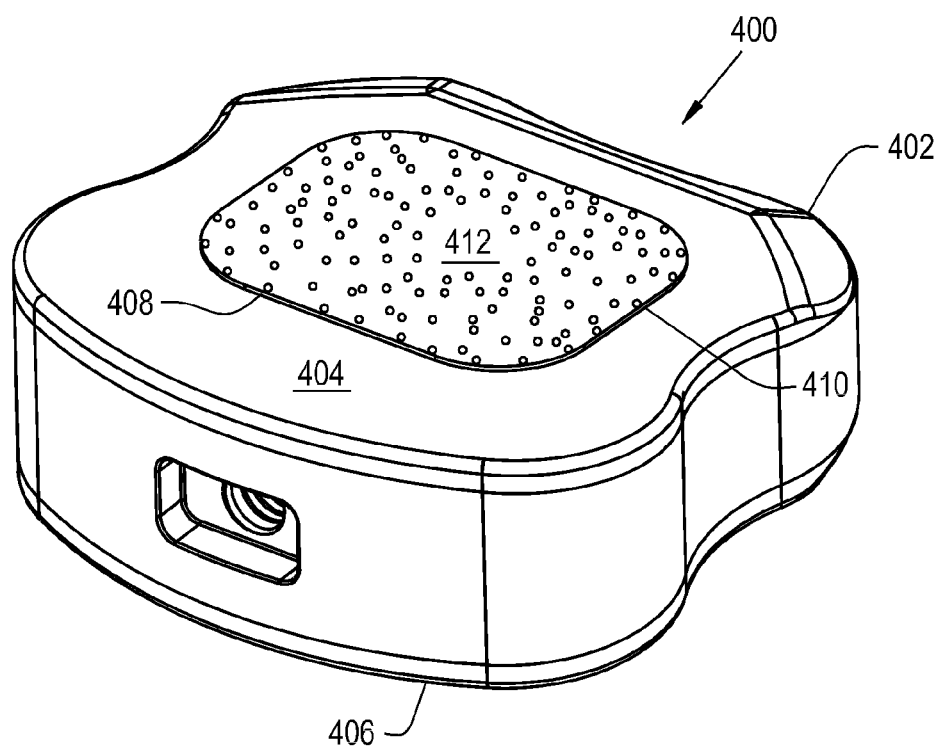
FIG. 36 is a perspective view of yet another embodiment of an orthopaedic implant according to the present invention.
Figure 37:
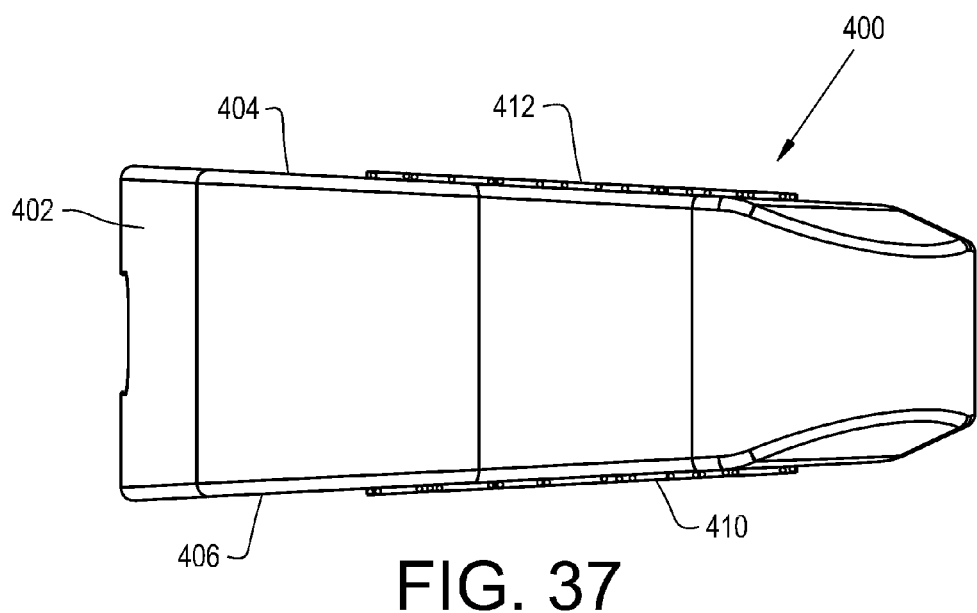
FIG. 37 is a side view of the orthopaedic implant shown in FIG. 36.

Referring now to FIGS. 36-37, another embodiment of an orthopaedic implant 400 according to the present invention is shown. The orthopaedic implant 400 includes an implant body 402, configured as an anterior lumbar interbody fusion cage, comprising a substantially non-porous material having a first surface 404, a second surface 406 opposite the first surface 404, and a cavity 408 that extends through the first surface 404 and second surface 406. As can be seen, the first surface 404 is a sloped planar surface that slopes downward from a front of the implant body 402 toward a back of the implant body 402. It should be appreciated that the slope of the first surface 404 can be adjusted, as desired, to provide a variety of shapes for the implant body 402 that are suitable for different surgical procedures.

A load bearing member 410 comprising a substantially porous material is held within the cavity 408. The load bearing member 410 has a first contact surface 412 that extends out of the cavity 408 and is proud of a portion of the first surface 404 to which the first contact surface 412 is immediately adjacent. Put another way, the first contact surface 412 outwardly projects from the cavity 408 so that it will contact surrounding anatomic features when the orthopaedic implant 400 is implanted and isolate portions of the first surface 404 immediately adjacent to the cavity 408 from initially bearing load from the surrounding anatomic features. Since the first surface 404 is sloped, the first contact surface 412 does not necessarily extend past a peak of the first surface 404, as previously described first contact surfaces do. However, in all other aspects, load bearing member 410 and first contact surface 412 can be configured similarly to previously described load bearing members and contact surfaces.

Figure 38:
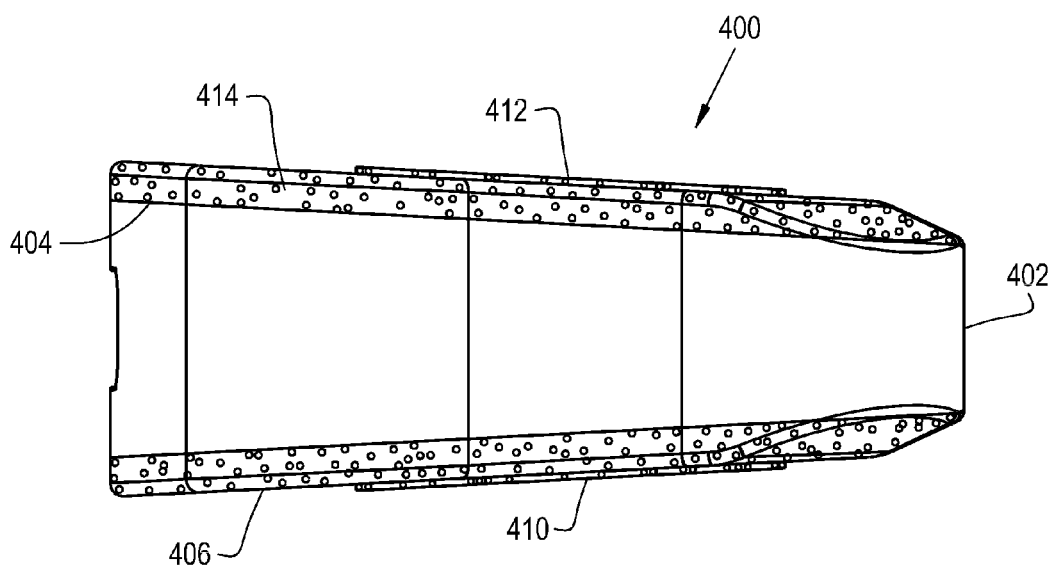
FIG. 38 is a side view of the orthopaedic implant shown in FIGS. 36-37 including an ingrowth material.

Referring now to FIG. 38, the orthopaedic implant 400 shown in FIGS. 36-37 is shown with an ingrowth material 414 covering the first surface 404 of the implant body 402. The ingrowth material 414 can be configured similarly to previously described ingrowth materials. As can be seen, the load bearing member 410 is proud of a portion of the ingrowth material 414 similarly to how the load bearing member 410 shown in FIGS. 36-37 is proud of a portion of the first surface 404.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic implant, comprising:
an implant body having a first surface with a first peak, a second surface opposite said first surface, and a cavity formed therein that extends through said first surface and said second surface, said implant body being substantially non-porous; and
a load bearing member comprising a substantially porous material held within said cavity, said load bearing member having a first contact surface extending out of said cavity past said first peak of said first surface and a second contact surface opposite said first contact surface, said load bearing member having interconnecting pores extending from said first contact surface to said second contact surface, said load bearing member having a total volume and said interconnecting pores in aggregate occupying at least 60% of said total volume.

2. The orthopaedic implant according to claim 1, wherein said first contact surface defines a thickness extending past said first surface.

3. The orthopaedic implant according to claim 2, wherein said thickness of said first contact surface relative to said first surface is constant throughout said first contact surface.

4. The orthopaedic implant according to claim 1, wherein said second surface of said implant body has a second peak, said second contact surface extending out of said cavity past said second peak.

5. The orthopaedic implant according to claim 1, wherein said load bearing member comprises at least one of polyether ether ketone (PEEK), tantalum, and titanium.

6. The orthopaedic implant according to claim 1, wherein said interconnecting pores in aggregate occupy at least 80% of said total volume.

7. The orthopaedic implant according to claim 1, wherein said implant body has a third surface with an opening formed therethrough to said cavity.

8. The orthopaedic implant according to claim 1, wherein said first surface defines a first surface area and said first contact surface defines a contact surface area, said first surface area and said contact surface area together defining a total surface area, said contact surface area being at least 40% of said total surface area.

9. The orthopaedic implant according to claim 1, further including an ingrowth material covering at least a portion of said first surface of said implant body and having an ingrowth peak, said first contact surface of said load bearing member extending out of said cavity past said ingrowth peak.

10. The orthopaedic implant according to claim 1, wherein said load bearing member substantially fills said cavity.

11. The orthopaedic implant according to claim 1, wherein said first contact surface is a planar surface.

12. The orthopaedic implant according to claim 1, wherein said implant body comprises at least one of PEEK, reinforced PEEK, titanium, stainless steel, cobalt chrome, and ultra-high molecular weight polyethylene.

13. An orthopaedic implant, comprising:
an implant body having a first surface, a second surface opposite said first surface, and a cavity formed therein that extends through said first surface and said second surface, said implant body being substantially non-porous; and
a load bearing member comprising a substantially porous material held within said cavity, said load bearing member having a first contact surface extending out of said cavity and being proud of a portion of said first surface, said load bearing member having a second contact surface opposite said first contact surface, said load bearing member having interconnecting pores extending from said first contact surface to said second contact surface, said load bearing member having a total volume and said interconnecting pores in aggregate occupying at least 60% of said total volume.

* * * * *